US006444447B1

(12) United States Patent
DeAngelis

(10) Patent No.: US 6,444,447 B1
(45) Date of Patent: Sep. 3, 2002

(54) POLYMER GRAFTING BY POLYSACCHARIDE SYNTHASES

(75) Inventor: Paul L. DeAngelis, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 09/437,277

(22) Filed: Nov. 10, 1999

Related U.S. Application Data

(63) Continuation-in-part of application No. 09/283,402, filed on Apr. 1, 1999.
(60) Provisional application No. 60/107,929, filed on Nov. 11, 1998.

(51) Int. Cl.$^7$ .......... C12P 19/18

(52) U.S. Cl. .......... 435/97; 435/72; 435/101
(58) Field of Search .......... 435/97, 72, 100, 435/101

(56) References Cited

U.S. PATENT DOCUMENTS

| | | | | | |
|---|---|---|---|---|---|
| 4,511,478 | A | | 4/1985 | Nowinski et al. | 210/691 |
| 4,615,697 | A | | 10/1986 | Robinson | 604/890 |
| 4,822,867 | A | | 4/1989 | Erhan | 527/200 |
| 4,983,392 | A | | 1/1991 | Robinson | 424/427 |
| 5,015,577 | A | * | 5/1991 | Weigel | 435/101 |
| 5,171,689 | A | | 12/1992 | Kawaguri et al. | 435/290 |
| 5,217,743 | A | | 6/1993 | Farah | 427/2 |
| 5,337,747 | A | | 8/1994 | Neftel | 128/635 |
| 5,472,704 | A | | 12/1995 | Santus et al. | 424/435 |
| 5,473,034 | A | | 12/1995 | Yasui et al. | 527/200 |
| 5,607,694 | A | | 3/1997 | Marx | 424/450 |
| 5,610,241 | A | | 3/1997 | Lee et al. | 525/411 |
| 5,631,019 | A | | 5/1997 | Marx | 424/450 |
| 5,651,982 | A | | 7/1997 | Marx | 424/450 |
| 5,711,959 | A | | 1/1998 | Kohler et al. | 424/423 |
| 5,837,747 | A | | 11/1998 | Soon-Shiong et al. | 522/26 |
| 5,885,609 | A | | 3/1999 | Amiji | 424/425 |
| 5,928,667 | A | | 7/1999 | Rosenblatt et al. | 424/484 |
| 5,945,457 | A | | 8/1999 | Plate et al. | 514/772.1 |
| 5,962,136 | A | | 10/1999 | Dewez et al. | 428/410 |
| 6,284,493 | B1 | * | 9/2001 | Roth | 435/72 |

FOREIGN PATENT DOCUMENTS

| | | |
|---|---|---|
| WO | WO95/24497 | 9/1995 |
| WO | WO97/20061 | 6/1997 |

OTHER PUBLICATIONS

Biomimetic Transport and Rational Drug Delivery, Ranney, et al., Biochemical Pharmacology, vol. 59, pp. 105–114, 2000.

Glycosidases and Glycosyl Transferases in Glycoside and Oligosaccharide Synthesis, Crout et al., Current Opinion in Chemical Biology, pp. 2:98–111, 1998.

Enzymological Characterization of the Pasteurella Multocida Hyaluronic Acid Synthase, DeAngelis, Biochemistry, vol. 35, No. 30, pp. 9768–9771, 1996.

Enzymatic Reconstruction of a Hybrid Glycosaminoglycan Containing 6–Sulfated, 4–Sulfated and Unsulfated N–Acetylgalactosamine, Takagaki, et al., Biochemical and Biophysical Research Communications 258, pp. 741–744, 1999.

Enzymic Reconstruction of Glycosaminoglycan Oligosaccharide Chains Using the Transglycosylation Reaction of Bovine Testicular Hyaluronidase, Saitoh, et al., The American Society for Biochemistry and Molecular Biology, Inc., vol. 127, No. 8, pp. 3741–3747, Feb. 24, 1995.

Chimeric Glycosaminoglycan Oligosaccharides Synthesized by Enzymatic Reconstruction and Their Use in Substrate Specificity Determination of Streptococcus Hyaluronidase, Takagaki, et al., J. Biochem. vol. 127, pp. 695–702, 2000.

Identification and Molecular Cloning of a Unique Hyaluronan Synthase from Pasteurella Multocida, DeAngelis, et al., J. Biol. Chem., vol. 273, Issue 14, pp. 8454–8458, 1998.

* cited by examiner

*Primary Examiner*—Nashaat T. Nashed
(74) *Attorney, Agent, or Firm*—Dunlap, Codding & Rogers, P.C.

(57) ABSTRACT

The present invention relates to methodology for polymer grafting by a polysaccharide synthase and, more particularly, polymer grafting using the hyaluronate synthase from *Pasteurella multocida*. The present invention also relates to coatings for biomaterials wherein the coatings provide protective properties to the biomaterial and/or act as a bioadhesive. Such coatings could be applied to electrical devices, sensors, catheters and any device which may be contemplated for use within a mammal. The present invention further relates to drug delivery matrices which are biocompatible and may comprise combinations of a biomaterial or a bioadhesive and a medicament or a medicament-containing liposome. The biomaterial and/or bioadhesive is a hyaluronic acid polymer produced by a hyaluronate synthase from *Pasteurella multocida*. The present invention also relates to the creation of chimeric molecules containing hyaluronic acid or hyaluronic acid-like chains attached to various compounds and especially carbohydrates or hydroxyl containing substances. The present invention also relates to a chondroitan synthase from *Pasteurella multocida* which is capable of producing polysaccharide polymers on an acceptor or primer molecule.

48 Claims, 11 Drawing Sheets

Figure 9

| Mutants | Enzyme Specific Activity | | |
|---|---|---|---|
| | HAS | GlcNAc-Tase | GlcUA-Tase |
| D477N | 4.7 % | 198.8 % | 2% |
| D477K | 0.15 % | 71.3 % | 1.8% |
| D477E | 7.1 % | 51.8% | 4.7 % |
| D196N | 0.1 % | 0 | 73.9 % |
| D196K | 0.01 % | 3.4 % | 98 % |
| D196E | 0.26 % | 6.75 % | 60 % |

POLYMER GRAFTING BY POLYSACCHARIDE SYNTHASES

CROSS-REFERENCE TO RELATED APPLICATIONS

This application claims the benefit of U.S. Provisional Application Ser. No. 60/107,929, filed Nov. 11, 1998, and is a continuation-in-part of U.S. patent application Ser. No. 09/283,402 entitled DNA Encoding Hyaluronan Synthase From *Pasteurella Multocida* and Methods, filed Apr. 1, 1999, both of which are hereby incorporated herein by reference.

STATEMENT REGARDING FEDERALLY SPONSORED RESEARCH OR DEVELOPMENT

Not applicable.

BACKGROUND

1. Field of the Invention

The present invention relates to methodology for polymer grafting by a polysaccharide synthase and, more particularly, polymer grafting using the hyaluronate synthase from *Pasteurella multocida*. The present invention also relates to coatings for biomaterials wherein the coatings provide protective properties to the biomaterial and/or act as a bioadhesive. Such coatings could be applied to electrical devices, sensors, catheters and any device which may be contemplated for use within a mammal. The present invention further relates to drug delivery matrices which are biocompatible and may comprise combinations of a biomaterial or a bioadhesive and a medicament or a medicament-containing liposome. The biomaterial and/or bioadhesive is a hyaluronic acid polymer produced by a hyaluronate synthase from *Pasteurella multocida*. The present invention also relates to the creation of chimeric molecules containing hyaluronic acid or hyaluronic acid-like chains or glycosaminoglycan chains attached to various compounds and especially carbohydrates or hydroxyl containing substances.

2. Description of the Related Art

Polysaccharides are large carbohydrate molecules composed from about 25 sugar units to thousands of sugar units. Animals, plants, fungi and bacteria produce an enormous variety of polysaccharide structures which are involved in numerous important biological functions such as structural elements, energy storage, and cellular interaction mediation. Often, the polysaccharide's biological function is due to the interaction of the polysaccharide with proteins such as receptors and growth factors. The glycosaminoglycan class of polysaccharides, which includes heparin, chondroitan, and hyaluronic acid, play major roles in determining cellular behavior (e.g. migration, adhesion) as well as the rate of cell proliferation in mammals. These polysaccharides are, therefore, essential for correct formation and maintenance of organs of the human body.

Several species of pathogenic bacteria and fungi also take advantage of the polysaccharide's role in cellular communication. These pathogenic microbes form polysaccharide surface coatings or capsules that are identical or chemically similar to host molecules. For instance, Group A & C Streptococcus and Type A *Pasteurella multocida* produce authentic hyaluronic acid capsules and pathogenic *Escherichia coli* are known to make capsules composed of polymers very similar to chondroitan and heparin. The pathogenic microbes form the polysaccharide surface coatings or capsules because such a coating is nonimmunogenic and protects the bacteria from host defenses thereby providing the equivalent of molecular camouflage.

Enzymes alternatively called synthases, synthetases, or transferases, catalyze the polymerization of polysaccharides found in living organisms. Many of the known enzymes also polymerize activated sugar nucleotides. The most prevalent sugar donors contain UDP but ADP, GDP, and CMP are also used depending on (1) the particular sugar to be transferred and (2) the organism. Many types of polysaccharides are found at or outside of, the cell surface. Accordingly, most of the synthase activity is typically associated with either the plasma membrane on the cell periphery or the Golgi apparatus membranes that are involved in secretion. In general, these membrane-bound synthase proteins are difficult to manipulate by typical procedures and only a few enzymes have been identified after biochemical purification.

A larger number of synthases have been cloned and sequenced at the nucleotide level using 'reverse genetic' approaches in which the gene or the complimentary DNA (cDNA) was obtained before the protein was characterized. Despite this sequence information, the molecular details concerning the three-dimensional native structures, the active sites, and the mechanisms of catalytic action of the polysaccharide synthases, in general, are very limited or absent. For example, the catalytic mechanism for glycogen synthesis is not yet known in detail even though the enzyme was discovered decades ago. In another example, it is still a matter of debate whether the enzymes that produce heteropolysaccharides utilize one UDP-sugar binding site to transfer both precursors, or alternatively, if there exists two dedicated regions for each substrate.

A wide variety of polysaccharides are commercially harvested from many sources, such as xanthan from bacteria, carrageenans from seaweed, and gums from trees. This substantial industry supplies thousands of tons of these raw materials for a multitude of consumer products ranging from ice cream desserts to skin cream cosmetics. Vertebrate tissues and pathogenic bacteria are the sources of more exotic polysaceharides utilized in the medical field as surgical aids, vaccines. and anticoagulants. For example, two glycosaminoglycan polysaccharides, heparin from pig intestinal mucosa and hyaluronic acid from rooster combs, are employed in several applications including clot prevention and eye surgery, respectively. Polysaccharides extracted from bacterial capsules (e.g. various *Streptococcus pneumoniae* strains) are utilized to vaccinate both children and adults against disease with varying levels of success. However, for the most part, one must use the existing structures found in the raw materials as obtained from nature. In many of the older industrial processes, chemical modification (e.g. hydrolysis, sulfation, deacetylation) is used to alter the structure and properties of the native polysaccharide. However, the synthetic control and the reproducibility of large-scale reactions are not always successful.

Some of the current methods for designing and constructing carbohydrate polymers in vitro utilize: (i) difficult, multistep sugar chemistry, or (ii) reactions driven by transferase enzymes involved in biosynthesis, or (iii) reactions harnessing carbohydrate degrading enzymes catalyzing transglycosylation. The latter two methods are restricted by the specificity and the properties of the available naturally occurring enzymes. Many of these enzymes are neither particularly abundant nor stable but are almost always expensive. Overall, the procedures currently employed yield polymers containing between 2 and about 12 sugars. Unfortunately, many of the physical and biological properties of polysaccharides do not become apparent until the polymer contains 25, 100, or even thousands of monomers.

As stated above, polysaccharides are the most abundant biomaterials on earth, yet many of the molecular details of their biosynthesis and function are not clear. Hyaluronic acid or "HA" is a linear polysaccharide of the glycosaminoglycan class and is composed of up to thousands of β(1,4)GlcUA-β(1,3)GlcNAc repeats. In vertebrates. HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as an(liogenesis, cancer, cell motility, wound healing, and cell adhesion.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

HA is also made by certain microbes that cause disease in humans and animals. Some bacterial pathogens, namely Gram-negative *Pasteurella multocidta* Type A and Gram-positive Streptococcus Group A and C, produce an extracellular HA capsule which protects the microbes from host defenses such as phagocytosis. Mutant bacteria that do not produce HA capsules are $10^2$- and $10^3$-fold less virulent in comparison to the encapsulated strains. Furthermore, the *Paramecium bursaria* chlorella virus (PBCV-1) directs the algal host cells to produce a HA surface coating early in infection.

The various HA synthases ("HAS"), the enzymes that polymerize HA, utilize UDP-GlcUA and UDP-GlcNAc sugar nucleotide precursors in the presence of a divalent Mn or Mg ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

HasA (or SpHAS) from Group A *Streptococcus pyogenes* was the first HA synthase to be described at the molecular level. The various vertebrate homologs (Xenopus frog DG42 or XlHAS1; murine and human HAS1, HAS2, and HAS3) and the viral enzyme, A98R, are quite similar at the amino acid level to certain regions of the HasA polypeptide chain (~30% identity overall). At least 7 short motifs (5–9 residues) interspersed throughout these enzymes are identical or quite conserved.

The evolutionary relationship among these HA synthases from such dissimilar sources is not clear at present. The enzymes are predicted to have a similar overall topology in the bilayer: membrane-associated regions at the amino and the carboxyl termini Sank a large cytoplasmic central domain (~200 amino acids). The amino terminal region appears to contain two transmembrane segments while the carboxyl terminal region appears to contain three to five membrane-associated or transmembrane segments depending on the species. Very little of these HAS polypeptide chains are expected to be exposed to the outside of the cell.

With respect to the reaction pathway utilized by this group of enzymes, mixed findings have been reported from indirect experiments. The Group A streptococcal enzyme was reported to add sugars to the nonreducing terminus of the growing chain as determined by selective labeling and degradation studies. Using a similar approach, however, two laboratories working with the enzyme preparations from mammalian cells concluded that the new sugars were added to the reducing end of the nascent chain. In comparing these various studies, the analysis of the enzymatically-released sugars from the streptococcal system added more rigorous support for their interpretation. In another type of experiment, HA made in mammalian cells was reported to have a covalently attached UDP group as measured by an incorporation of low amounts of radioactivity derived from $^{32}$P-labeled UDP-sugar into an anionic polymer. This data implied that the last sugar was transferred to the reducing end of the polymer. Thus, it remains unclear if these rather similar HAS polypeptides from vertebrates and streptococci actually utilize different reaction pathways.

To facilitate the development of biotechnological medical improvements, the present invention provides a method to apply a surface coating of HA that will shield the artificial components or compounds from the detrimental responses of the body as well as encourage engrafting of a foreign medical device within living tissue. Such a coating of HA will bridge the gap between man-made substances and living flesh (i.e. improve biocompatibilty). The HA can also be used as a biomaterial such as a biodhesive or a bioadhesive containing a medicament delivery system, such as a liposome, and which is non-immunogenic. The present invention also encompasses the methodology of polysaccharide polymer grafting, i.e. HA or chondroitan, using either a hyaluronate synthase (PmHAS) or a chondroitan synthase (PmCS) from *P. multocida*. Modified versions of the PmHAS or PmCS enzymes (genetic or chemical) can also be utilized to graft on polysaccharides of various size and composition.

SUMMARY OF THE INVENTION

A unique HA synthase, PmHAS, from the fowl cholera pathogen, Type A *P. multocida* has been identified and cloned and is disclosed and claimed in co-pending U.S. Ser. No. 09/283,402, filed Apr. 1, 1999, and entitled "DNA Encoding Hyaluronan Synthase From *Pasteurella Multocida* and Methods," the contents of which are hereby expressly incorporated herein. Expression of this single 972-residue protein allows *Escherichia coli* host cells to produce HA capsules in vivo; normally *E. coli* does not make HA. Extracts of recombinant *E. coli.*, when supplied with the appropriate UDP-sugars, make HA in vitro. Thus, the PmHAS is an authentic HA synthase.

It has also been determined that the PmHAS adds sugars to the nonreducing end of a growing polymer chain. The correct monosaccharides are added sequentially in a stepwise fashion to the nascent chain or a suitable exogenous HA oligosaccharide. The PmHAS sequence, however, is significantly different from the other known HA synthases. There appears to be only two short potential sequence motifs ([D/N]DGS[S/T]; DSD[D/T]Y) in common between PmHAS and the Group A HAS—HasA. Instead, a portion of the central region of the new enzyme is more homologous to the amino termini of other bacterial glycosyltransferases that produce different capsular polysaccharides or lipopolysaccharides. Furthermore, even though PmHAS is about twice as long as any other HAS enzyme, it only has two predicted transmembrane spanning helices separated by ~320 residues. Thus at least a third of the polypeptide is predicted not to be in the cytoplasm.

When the PmHAS is given long elongation reaction times, HA polymers of at least 400 sugars long are formed. Unlike any other known HAS enzyme, PmHAS also has the ability to extend exogenously supplied short HA oligosaecharides into long HA polymers in vitro. If enzyme is supplied with these short HA oligosaceharides, total HA biosynthesis is increased up to 50-fold over reactions without the exogenous oligosaccharide. The nature of the polymer retention mechanism of the PmHAS polypeptide might be the causative factor for this activity: i.e. a HA-binding site may exist that holds onto the HA chain during polymerization. Small HA oligosaceharides also, are capable of occupying this site of the recombinant enzyme and thereafter be extended into longer polysaccharide chains.

Most membrane proteins are relatively difficult to study due to their insolubility in aqueous solution, and the HASs are no exception. Only the enzyme from Group A and C Streptococcus bacteria has been detergent-solubilized and purified in an active state in small quantities. Once isolated in a relatively pure state, the streptococcal enzyme has very limited stability. A soluble recombinant form of the enzyme from *P. multocida* called PmHAS-D which comprises residues 1–703 of the 972 residues of the native PmHAS enzyme, the amino acid sequence of PmHAS-D is shown in SEQ ID NO:1 with the nucleotide sequence of PmHAS-D is shown in SEQ ID NO:2. PmHAS-D can be mass-produced in *E. coli* and purified by chromatography. The PmHAS-D enzyme retains the ability of the parent enzyme to add on a long HA polymer onto short HA primers. Furthermore, the purified PmHAS-D enzyme is stable in an optimized buffer for days on ice and for hours at normal reaction temperatures. One formulation of the optimal buffer consists of 1M ethylene glycol, 0.1–0.2 M ammonium sulfate, 50 mM Tris, pH 7.2, and protease inhibitors which allows the stability and specificity at typical reaction conditions for sugar transfer. For the reaction UDP-sugars and manganese (10–20 mM) are added. PmHAS-D will also add on a HA polymer onto plastic beads with an immobilized short HA primer.

The present invention encompasses methods of producing a variety of unique biocompatible molecules and coatings based on polysaccharides. Polysaccharides, especially those of the glycosaminoglycan class, serve numerous roles in the body as structural elements and signaling molecules. By grafting or making hybrid molecules composed of more than one polymer backbone, it is possible to meld distinct physical and biological properties into a single molecule without resorting to unnatural chemical reactions or residues.

The present invention also incorporates the propensity of certain recombinant enzymes, when prepared in a virgin state, to utilize various acceptor molecules as the seed for further polymer growth: naturally occurring forms of the enzyme or existing living host organisms do not display this ability. Thus, the present invention results in (a) the production of hybrid polysaccharides and (b) the formation of polysaccharide coatings. Such hybrid polymers can serve as "molecular glue"—i.e. when two cell types or other biomaterials interact with each half of a hybrid molecule, then each of the two phases are bridged.

Such polysaccharide coatings are useful for integrating a foreign object within a surrounding tissue matrix. For example, a prosthetic device is more firmly attached to the body when the device is coated with a naturally adhesive polysaccharide. Additionally, the devices artificial components could be masked by the biocompatible coating to reduce immunoreactivity or inflammation. Another aspect of the present invention is the coating or grafting of HA onto various drug delivery matrices or bioadhesives or suitable medicaments to improve and/or alter delivery, half-life, persistence, targeting and/or toxicity.

DESCRIPTION OF THE DRAWINGS

FIG. 9 is a tabular representation showing enzyme activity of the PmHAS-D mutants.

DETAILED DESCRIPTION OF THE INVENTION

Figure 1:
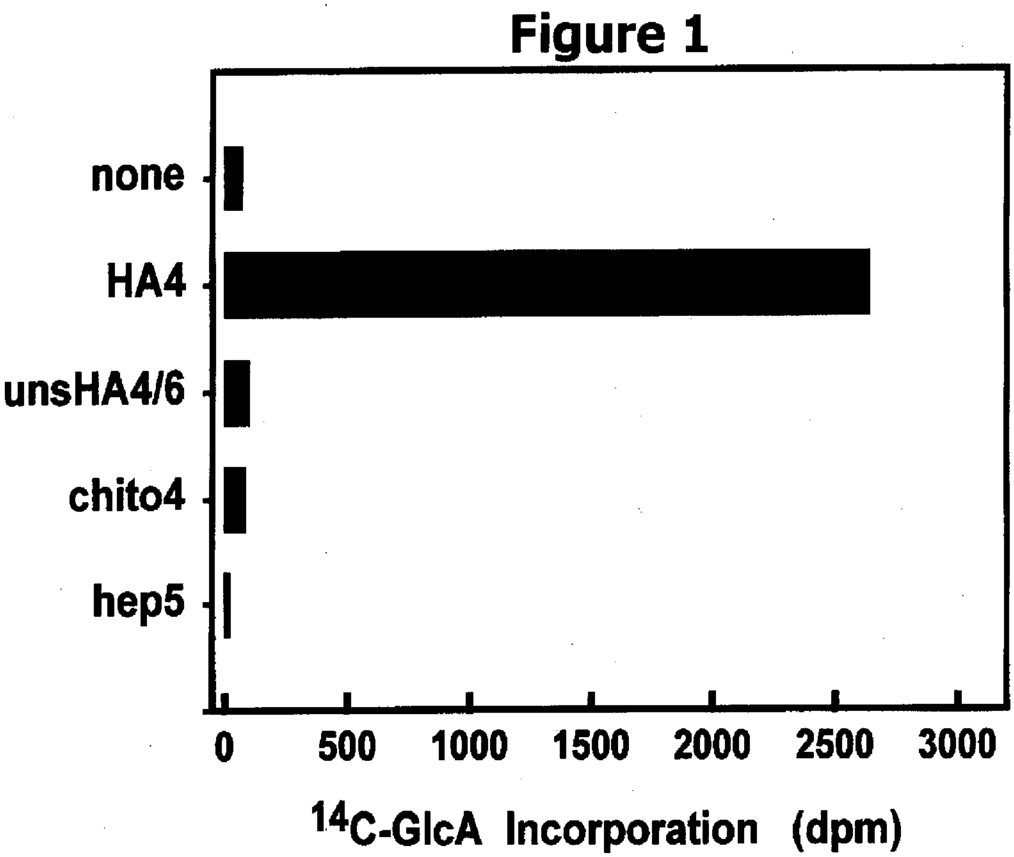
FIG. 1 is a graphical representation showing that an HA tetramer stimulates PmHAS polymerization.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence or Chondroitin Synthase ("CS") coding sequence yet is isolated away from, or purified free from, unrelated genomic DNA, for example, total *Pasteurella multocida*. Included within the term "DNA segment", are DNA segments and smaller fragments of such segments, and also recombinant vectors, including, for example, plasmids, cosmids, phage, viruses, and the like.

Similarly, a DNA segment comprising an isolated or purified PmHAS-D or PmCS gene refers to a DNA segment including HAS or chondroitin synthase coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest. in this case PmHAS-D or PmCS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HAS or chondroitin synthase gene from the prokaryote *P. multocida*. One such advantage is that, typically, eukaryotic enzymes may require significant post-translational modifications that can only be achieved in a eukaryotic host. This will tend to limit the applicability of any eukaryotic HAS or chondroitin synthase gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the PmHAS-D or PmCS gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a PmHAS-D or PmCS gene, that includes within its amino acid sequence an amino acid sequence in accordance with SEQ ID NO:1 or 3, respectively. Moreover, in other particular embodiments, the invention concerns isolated DNA segments and recombinant vectors incorporating DNA sequences which encode a gene that includes within its amino acid sequence the amino acid sequence of an HAS or chondroitin synthase gene or DNA, and in particular to an HAS or chondroitin synthase gene or cDNA, corresponding to *Pasteurella multocida* HAS or chondroitin synthase. For example, where the DNA segment or vector encodes a full length HAS or chondroitin synthase protein. or is intended for use in expressing the HAS or chondroitin synthase protein, preferred sequences are those which are essentially as set forth in SEQ ID NO:1 or 3, respectively.

Truncated PmHAS-D also falls within the definition of preferred sequences as set forth in SEQ ID NO:1. For instance, at the carboxyl terminus, approximately 270–272 amino acids may be removed from the sequence and still have a functioning HAS. Those of ordinary skill in the art would appreciate that simple amino acid removal from either end of the PmHAS-D sequence can be accomplished. The truncated versions of the sequence simply have to be checked for HAS activity in order to determine if such a truncated sequence is still capable of producing HAS.

Nucleic acid segments having HAS or chondroitin synthase activity may be isolated by the methods described herein. The term "a sequence essentially as set forth in SEQ ID NO:X means that the sequence substantially corresponds to a portion of SEQ ID NO:X and has relatively few amino acids which are not identical to, or a biologically functional equivalent of, the amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a hyaluronic acid coat or chondroitin. In the above examples "X" refers to either SEQ ID NO: 1, 2, 3, or 4.

The art is replete with examples of practitioners ability to make structural changes to a nucleic acid segment (i.e. encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019–1029 (1988) [". . . according to the observed exchangeability of amino acid side chains, only four groups could be delineated; (i) lie and Val; (ii) Leu and Met, (iii) Lys, Arg, and (Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481–497 (1991) [similarity parameters allow amino acid substitutions to be designed]; and (3) Overington et al. "Environment-Specific Amino Acid Substitution fables: Tertiary Templates and Prediction of Protein Folds," Protein Science 1:216–226 (1992) ["Analysis of the pattern of observed substitutions as a function of local environment shows that there are distinct patterns . . . " Compatible changes can be made.]

These references and countless others, indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding an enzymatically active HAS or chondroitin synthase from *P. multocida*—PmHAS and PmCS, respectively. One of ordinary skill in the art would appreciate that substitutions can be made to the PmHAS or PmCS nucleic acid segment listed in SEQ ID NO:2 and 4, respectively, without deviating outside the scope and claims of the present invention. Standardized and accepted functionally equivalent amino acid substitutions are presented in Table 1.

TABLE I

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |

TABLE I-continued

| Amino Acid Group | Conservative and Semi-Conservative Substitutions |
|---|---|
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine Histidine |

Another preferred embodiment of the present invention is a purified nucleic acid segment that encodes a protein in accordance with SEQ ID NO:1 or 3,respectively, further defined as a recombinant vector. As used herein, the term "recombinant vector" refers to a vector that has been modified to contain a nucleic acid segment that encodes an HAS or chondroitin synthase protein, or fragment thereof: The recombinant vector may be further defined as an expression vector comprising a promoter operatively linked to said HAS encoding nucleic acid segment.

A further preferred embodiment of the present invention is a host cell, made recombinant with a recombinant vector comprising an HAS or chondroitin synthase gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding HAS or chondroitin synthase, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

In preferred embodiments, the HAS or chondroitin synthase encoding DNA segments further include DNA sequences. known in the art functionally as origins of replication or "replicons", which allow replication of contiguous sequences by the particular host. Such origins allow the preparation of extrachromosomally localized and replicating chimeric segments or plasmids, to which HAS or chondroitin synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HAS or chondroitin synthase coding gene sequence together with an appropriate replication origin and under the control of selected control regions.

Thus, it will be appreciated by those of skill in the art that other means may be used to obtain the HAS or chondroitin synthase gene or cDNA, in light of the present disclosure. For example, polymerase chain reaction or RT-PCR produced DNA fragments may be obtained which contain full complements of genes or cDNAs from a number of sources, including other strains of Pasteurella or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both Lactococcus or Bacillus strains and *E. coli* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade Lactococcus or Bacillus strain for production of HA or chondroitin. These are benign and well studied organisms used in the production of certain foods and biotechnology products. These are advantageous in that one can augment the Lactococcus or Bacillus strain's ability to synthesize HA or chondroitin through gene dosaging (i.e., providing extra copies of the HAS or chondroitin synthase gene by amplification) and/or inclusion of additional genes to increase the availability of HA or chondroitin precursors. The inherent ability of a bacterium to synthesize HA or chondroitin can also be augmented through the formation of extra copies, or amplification, of the plasmid that carries the HAS or chondroitin synthase gene. This amplification can account for up to a 10-fold increase in plasmid copy number and, therefore, the HAS or chondroitin synthase gene copy number.

Another procedure that would further augment HAS or chondroitin synthase gene copy number is the insertion of multiple copies of the gene into the plasmid. Another technique would include integrating the HAS or chondroitin synthase gene into chromosomal DNA. This extra amplification would be especially feasible, since the bacterial HAS or chondroitin synthase gene size is small. In some scenarios, the chromosomal DNA-ligated vector is employed to transfect the host that is selected for clonal screening purposes such as *E. coli*, through the use of a vector that is capable of expressing the inserted DNA in the chosen host.

In certain other embodiments, the invention concerns isolated DNA segments and recombinant vectors that include within their sequence a nucleic acid sequence essentially as set forth in SEQ ID NO:1, 2, 3 or 4. The term "essentially as set forth" in SEQ ID NO:1, 2, 3, or 4 is used in the same sense as described above and means that the nucleic acid sequence substantially corresponds to a portion of SEQ ID NO:1, 2, 3 or 4 and has relatively few codons which are not identical, or functionally equivalent, to the codons of SEQ ID NO:1, 2, 3 or 4. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional—or C-terminal amino acids or 5' or 3' nucleic acid sequences, and yet still be essentially as set forth in one of the sequences disclosed herein, so long as the sequence meets the criteria set forth above, including the maintenance. of biological protein activity where protein expression and enzyme activity is concerned. the addition of terminal sequences particularly applies to nucleic acid sequences which may, for example, include various non-coding sequences flanking either of the 5' or 3' portions of the coding region or may include various internal sequences, which are known to occur within genes. Furthermore, residues may be removed from the N or C terminal amino acids and yet still be essentially as set forth in one of the sequences disclosed herein, so long as the sequence meets the criteria set forth above, as well.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NO:2 or 4 will be sequences which are "essentially as set forth" in SEQ ID NO:2 or 4. Sequences which are essentially the same as those set forth in SEQ ID NO:2 or 4 may also be functionally defined as sequences which are capable of hybridizing to a nucleic acid segment containing the complement of SEQ ID NO:2 or 4 under standard or less stringent hybridizing conditions. Suitable standard hybridization conditions will be well known to those of skill in the art and are clearly set forth herein.

The term "standard hybridization conditions" as used herein. is used to describe those conditions under which substantially complementary nucleic acid segments will form standard Watson-Crick base-pairing. A number off actors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for hybridization will include 1.2–1.8×HPB at 40–50° C.

Naturally, the present invention also encompasses DNA segments which are complementary, or essentially complementary, to the sequences set forth in SEQ ID NO:2 or 4. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:2 or 4.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular amino acid and nucleic acid sequences of SEQ ID NO:1, 2, 3, and 4. Recombinant vectors and isolated DNA segments may therefore variously include the HAS or chondroitin synthase coding regions themselves, coding regions bearing selected alterations or modifications in the basic coding region, or they may encode larger polypeptides which nevertheless include HAS or chondroitin synthase-coding regions or may encode biologically functional equivalent proteins or peptides which have variant amino acids sequences.

The DNA segments of the present invention encompass biologically functional equivalent HAS or chondroitin synthase proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS or chondroitin synthase protein or to test HAS or chondroitin synthase mutants in order to examine HAS or chondroitin synthase activity at the molecular level.

Traditionally, chemical or physical treatments of polysaccharides were required to join two dissimilar materials. For example, a reactive nucleophile group of one polymer or surface was exposed to an activated acceptor group of the other material. Two main problems exist with this approach. however. First, the control of the chemical reaction cannot be refined and differences in temperature and level of activation often result in a distribution of several final products that vary from lot to lot preparation. For instance, several chains may be cross-linked in a few random, ill-defined areas and the resulting sample is not homogenous. Second, the use of chemical reactions to join molecules often leaves an unnatural or nonbiological residue at the junction of biomaterials. For example, the use of an amine and an activated carboxyl group would result in an amide linkage. This inappropriate residue buried in a carbohydrate may pose problems with biological systems such as degradation products which accumulate to toxic levels or may trigger an immune response.

Most polysaccharide polymers must be of a certain length before their physical or biological properties become apparent. Often the polysaccharide must comprise at least 20–100 sugar units. Certain enzymes that react with exogenous polymers have been previously available, but typically add only one sugar unit. The unique enzyme described in the present invention, PmHAS, forms polymers of at least 100–400 sugar units in length. The present invention thus results in long, defined linear polymers composed of only natural glycosidic linkages.

The two known glycosaminoglycan synthesizing enzymes from *Pasteurella multocida* bacteria normally make polymers similar to or identical to vertebrate polymers. These bacteria employ the polysaccharide, either HA (Type A bacteria) or chondroitin (Type F bacteria), as an extracellular coating to serve as molecular camouflage. Native enzymes normally make polymer chains of a single type of sugar repeat. If a recombinant HA synthase enzyme is employed, however, the enzyme can be forced to work on an exogenous acceptor molecule. For instance, the recombinant enzyme may be incubated with a polymer acceptor and the recombinant enzyme will then elongate the acceptor with UDP-sugar precursors. The known native enzymes do not perform this reaction since they already contain a growing polymer chain.

PmHAS, a 972 amino acid residue protein from *Pasteurella multocida*, is made in recombinant *Escherichia coli*. Other functional derivatives of PmHAS, for example an enzyme called PmHAS-D, have been produced which are soluble. The soluble form can be prepared in larger quantities and in a purer state than the naturally -occurring full-length enzyme. The preferred *E. coli* strains do not have an UDP-Glc dehydrogenase and therefore the recombinant enzyme does not make a HA chain in the foreign host. Therefore the enzyme is in a "virgin" state since the empty acceptor site can be occupied with foreign polymers. For example, the recombinant enzyme may be incubated in a mixture containing 50 mM Tris pH 7.2, 20 mM $MnCl_2$, 150–1600 $\mu$M UDP-GlcA, 200–1500 $\mu$M UDP-GlcNAc, and a suitable acceptor at 30° C. for 30–180 minutes. Suitable acceptors can be short HA chains (two or more sugar units) or short chondroitin sulfate chains (5 sugar units) or long chondroitin sulfate chains (~$10^2$ sugar units). In the case of the latter two acceptors, the PmHAS, and its derivatives, then elongates the foreign acceptors (i.e. long or short chondroitan oligosaccharides) at their nonreducing termini with authentic HA chains of up to 400 sugars. The A; length of the HA chain added onto the acceptor is controlled by altering the concentration of UDP-sugars and/or the reaction time. Immobilized acceptors, such as beads or other solid objects with bound acceptor oligosaccharides, can also be extended by the PmHAS enzyme using UDP-sugars. In this manner, the PmHAS enzyme can be used to attach polysaccharide chains to any suitable acceptor molecule.

Type A *P. multocida* produces a HA capsule [GlcUA-GlcNAc repeats] and possesses the PmHAS enzyme. On the other hand, Type F P. multocida produce a chondroitan or chondroitan-like polymer capsule [GlcUA-GalNAc repeats]. The DNA encoding an open reading frame (GenBank accession #AF 195517) that is 87% identical to PmHAS at the protein level has been cloned; this new enzyme is called PmCS, the *P. multocida* chondroitan synthase. The amino acid sequence of PmCS is set forth in SEQ ID NO:3 and the PmCS nucleotide sequence is set forth in SEQ ID NO:4. As the PmCS enzyme's sequence is so similar to PmHAS, one of ordinary skill in the art would be able to manipulate the PmCS in the same manner as that for PmHAS and any manipulation that was successful with regard to the PmHAS would be performable with the PmCS, with the exception that chondroitan chains would be grafted instead of HA. Either HA or chondroitan chains can serve as acceptors for PmCS as both acceptors serve well for PmHAS.

Such a hybrid polysaccharide material composed of both HA and chondroitin cannot be formed by any other existing process without (1) leaving unnatural residues and/or (2) producing undesirable crosslinking reactions. The hybrid polysaccharide material can serve as a biocompatible molecular glue for cell/cell interactions in artificial tissues or organs and the HA/chondroitin hybrid mimics natural proteoglycans that normally contain an additional protein intermediate between polymer chains. The present invention, therefore, obviates the requirement for a protein intermediary. A recombinant HA/chondroitin hybrid polysaccharide, devoid of such an intermediary protein, is desirous since molecules from animal sources are potentially immunogenic—the hybrid polysaccharide, however, would not appear as "foreign" to the host, thus no immune response is generated.

An intrinsic and essential feature of polysaccharide synthesis is the repetitive addition of sugar monomer units to the growing polymer. The glycosyltransferase is expected to remain in association with the nascent chain. This feature is particularly relevant for HA biosynthesis as the HA polysaceharide product. in all known cases, is transported out of the cell; if the polymer was released, then the HAS would not have another chance to elongate that particular molecule. Three possible mechanisms for maintaining the growing polymer chain at the active site of the enzyme are immediately obvious. First, the enzyme possesses a carbohydrate polymer binding pocket or cleft. Second, the nascent chain is covalently attached to the enzyme during its synthesis. Third, the enzyme binds to the nucleotide base or the lipid moiety of the precursor while the nascent polymer chain is still covalently attached.

The HAS activity of the native PmHAS enzyme found in *P. multocida* membrane preparations is not stimulated by the addition of HA oligosaccharides; theoretically, the endogenous nascent HA chain initiated in vivo renders the exogenously supplied acceptor unnecessary. However, recombinant PmHAS produced in an *E. coli* strain that lacks the UDP-GlcUA precursor, and thus lacks a nascent HA chain, is able to bind and to elongate exogenous HA oligosacеharides. As mentioned above, there are three likely means for a nascent HA chain to be held at or near the active site. In the case of PmHAS, it appears that a HA-binding site exists near or at the sugar transferase catalytic site.

Defined oligosaccharides that vary in size and composition are used to discern the nature of the interaction between PmHAS and the sugar chain. For example, it appears that the putative HA-polymer binding pocket of PmHAS will bind and elongate at least an intact HA trisaccharide (reduced tetramer). The monosaccharides GlcUA or GlcNAc, however, even in combination at high concentration, are not effective acceptors. Oligosaecharide binding to PmHAS appears to be somewhat selective because the heparosan pentamer, which only differs in the glycosidic linkages from HA-derived oligosaccharides, does not serve as an acceptor. However, chondroitan [GlcUA-GalNAc repeat] does serve as an acceptor for PmHAS.

To date, no other HA synthase besides PmHAS has been shown to utilize an exogenous acceptor or primer sugar. In an early study of a cell-free HA synthesis system, preparations of native Group A streptococcal HAS were neither inhibited nor stimulated by the addition of various HA oligosaccharides including the HA tetramer derived from testicular hyaluronidase digests. These membrane preparations were isolated from cultures that were producing copious amounts of HA polysaccharide. The cells were hyaluronidase-treated to facilitate handling. Therefore, it is quite likely that the native streptococcal enzyme was isolated with a small nascent HA chain attached to or bound to the protein much as suspected in the case of the native PmHAS. Theoretically, the, existing nascent chain formed in vivo would block the entry and subsequent utilization of an exogenous acceptor by the isolated enzyme in vitro. With the advent of molecularly cloned HAS genes, it is possible to prepare virgin enzymes lacking a nascent HA chain if the proper host is utilized for expression.

Both heparin and chondroitin, in mammalian systems, are synthesized by the addition of sugar units to the nonreducing end of the polymer chain. In vivo, the glycosyltransferases initiate chain elongation on primer tetrasaccharides [xylose-galactose-galactose-GlcUA] that are attached to serine residues of proteoglycan core molecules. In vitro, enzyme extracts transfer a single sugar to exogenously added heparin or chondroitin oligosaccharides; unfortunately, the subsequent sugar of the disaccharide unit is usually not added and processive elongation to longer polymers does not occur. Therefore it is likely that some component is altered or missing in the in vitro system. In the case of heparin biosynthesis, it is postulated that a single enzyme transfers both GlcUA and GlcNAc sugars to the glycosaminoglycan chain based on co-purification or expression studies.

Recent work with the *E. coli* K5 KfiC enzyme, which polymerizes heparosan, indicates that a single protein can transfer both sugars to the nonreducing end of acceptor molecules in vitro. Processive elongation, however, was not demonstrated in these experiments; crude cell lysates transferred a single sugar to defined even- or odd-numbered oligosaccharides. However, their initial mutagenesis experiments suggest that at least two independent sites are involved in transfer of the two monosaccharides.

Recombinant PmHAS adds single monosaccharides in a sequential fashion to the nonreducing termini of the nascent HA chain. Elongation of HA polymers containing hundreds of sugars has been demonstrated in vitro. The simultaneous formation of the disaccharide repeat unit is not necessary for generating the alternating structure of the HA molecule. The intrinsic specificity and fidelity of each half-reaction (e.g. GlcUA added to a GlcNAc residue or vice versa) apparently is sufficient to synthesize authentic HA chains.

A great technical benefit resulting from the alternating disaccharide structure of HA is that the reaction can be dissected by controlling the availability of UDP-sugar nucleotides. By omitting or supplying precursors in a reaction mixture, the glycosyltransferase may be stopped and started at different stages of synthesis of the heteropolysaccharide. In contrast, there is no facile way to control in a step-wise fashion the glycosyltransferase enzymes that produce important homopolysaccharides such as chitin, cellulose, starch, and glycogen.

An alternative method for controlling polymerization has been accomplished by creating mutants that only add one sugar linkage onto a short HA oligosaccharide. For example, PmHAS-E [PmHAS residues 1–650] can only add single GlcNAc sugars onto the non-reducing end (i.e. HA tetrasaccharide [GlcNAc-GlcUA-GlcNAc-GlcUA]) of an acceptor (i.e. forms the HA pentamer). On the other hand, a mutant has been created and called PmHAS-D-D477N [PmHAS residues 1–703 with an asparagine substituted for the aspartate at position 477], which transfers only a single GlcUA residue onto the non-reducing terminal GlcNAc group of the short HA oligosaccharide. If extracts of two such mutants are mixed together with an acceptor in the presence of UDP-GlcNAc and UDP-GlcUA, then significant polymerization is achieved. It is also obvious that by carrying out the steps of GlcNAc or GlcUA transfer separately and sequentially, almost any HA chain length should be possible. The same is also true with regard to PmCS either alone or in combination with PmHAS.

As stated above, membrane preparations from recombinant .*E coli* containing a PmHAS protein had HA synthase activity as judged by incorporation of radiolabel from UDP-[$^{14}$C]GlcUA into polymer when co-incubated with both UDP-GlcNAc and Mn ion. Due to the similarity at the amino acid level of PmHAS to several lipopolysaccharide transferases, it was hypothesized that HA oligosaccharides serve as acceptors for GlcUA and GlcNAc transfer. Addition of unlabeled even-numbered HA tetramer (from testicular hyaluronidase digests) to reaction mixtures with recombinant PmHAS stimulates incorporation of radiolabel from UDP-[$^{14}$C]GlcUA into HA polymer by ~20- to 60-fold in comparison to reactions without oligosaccharides as shown in FIG. 1.

In FIG. 1, a series of reactions containing PmHAS (30 $\mu$g total membrane protein) were incubated with UDP-[$^{14}$C]GlcUA (2×10 dpm, 120 $\mu$M) and UDP-GlcNAc (450 $\mu$M) in assay buffer (50 $\mu$l reaction vol) in the presence of no added sugar (none) or various oligosaccharides (HA4, 4 $\mu$g HA tetramer; unsHA4/6, 4 $\mu$g unsaturated HA Δtetramer and Δhexamer; chito4, 50 $\mu$g chitotetraose; hep5, 20 $\mu$g heparosan pentamer). After 1 hour, the reactions were analyzed by descending paper chromatography. Incorporation of radiolabel from UDP-[$^{14}$C]GlcUA into high molecular weight HA is shown. Only intact tetramer (HA4) served as an acceptor. Reactions with heparosan and chitooligosaccharides, as well as GlcNAc and/or GlcUA (not shown), incorporated as much radiolabel as parallel reactions with no acceptor. The free monosaccharides GlcUA and GlcNAc, either singly or in combination at concentrations of up to 100 $\mu$M, do not serve as acceptors; likewise, the beta-methyl glycosides of these sugars do not stimulate HAS activity.

In the same manner, PmHAS has been shown to add sugars onto a chondroitan pentamer acceptor. The PmHAS and reagents were prepared in the same manner as shown in FIG. 1, except that a chondroitan pentamer was used as the acceptor molecule. The results of this experiment are shown in TABLE A.

TABLE A

| Sugar | mass | Incorporation of $^{14}$C-GlcUA dpm |
|---|---|---|
| none | — | 60 |
| $HA_4$ | 5 $\mu$g | 2,390 |
| Chondroitan Pentamer | 20 $\mu$g | 6,690 |

Thus, it can be seen that the PmHAS can utilize numerous acceptors or primer molecules as the basis for forming a polysaccharide polymer chain.

Figure 2:
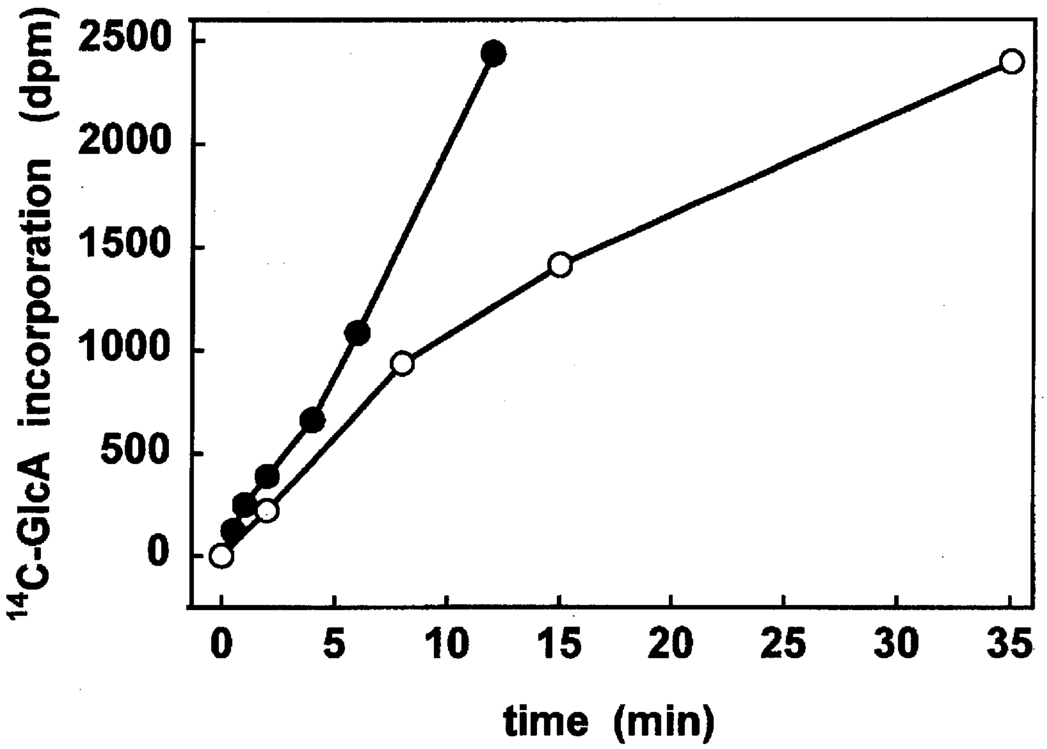
FIG. 2 is a graphical plot showing that HA polymerization is effected by HA oligosaccharides.

The activity of recombinant PmHAS is dependent on the simultaneous incubation with both UDP-sugar precursors and a $Mn^{2+}$ ion. The level of incorporation is dependent on protein concentration, on HA oligosaccharide concentration, and on incubation time as shown in FIG. 2. In FIG. 2, two parallel reactions containing PmHAS with even-numbered HA oligosaccharides (105 $\mu$g membrane protein/point with a mixture of HA hexamer, octamer, and decamer, 4.4. $\mu$g total; solid circles) or six-fold more PmHAS without oligosaccharide acceptor (630 $\mu$g protein/point; open circles) were compared. The enzyme preparations were added to prewarmed reaction mixtures containing UDP-[$^{14}$C]GlcUA (240 $\mu$M 6×$10^4$ dpm/point) and UDP-GlcNAc (600 $\mu$M) in assay buffer. At various times, 50 $\mu$l aliquots were withdrawn, terminated, and analyzed by paper chromatography. The exogenously supplied acceptor accelerated the bulk incorporation of sugar precursor into polymer product by PmHAS, but the acceptor was not absolutely required.

HA synthesized in the presence or the absence of HA oligosaccharides is sensitive to HA lyase (>95% destroyed) and has a molecular weight of ≧1–5×$10^4$ Da (50–250 monosaccharides). No requirement for a lipid-linked intermediate was observed as neither bacitracin (0.5 mg/ml) nor tunicamycin (0.2 mg/ml) alter the level of incorporation in comparison to parallel reactions with no inhibitor.

Figure 3:
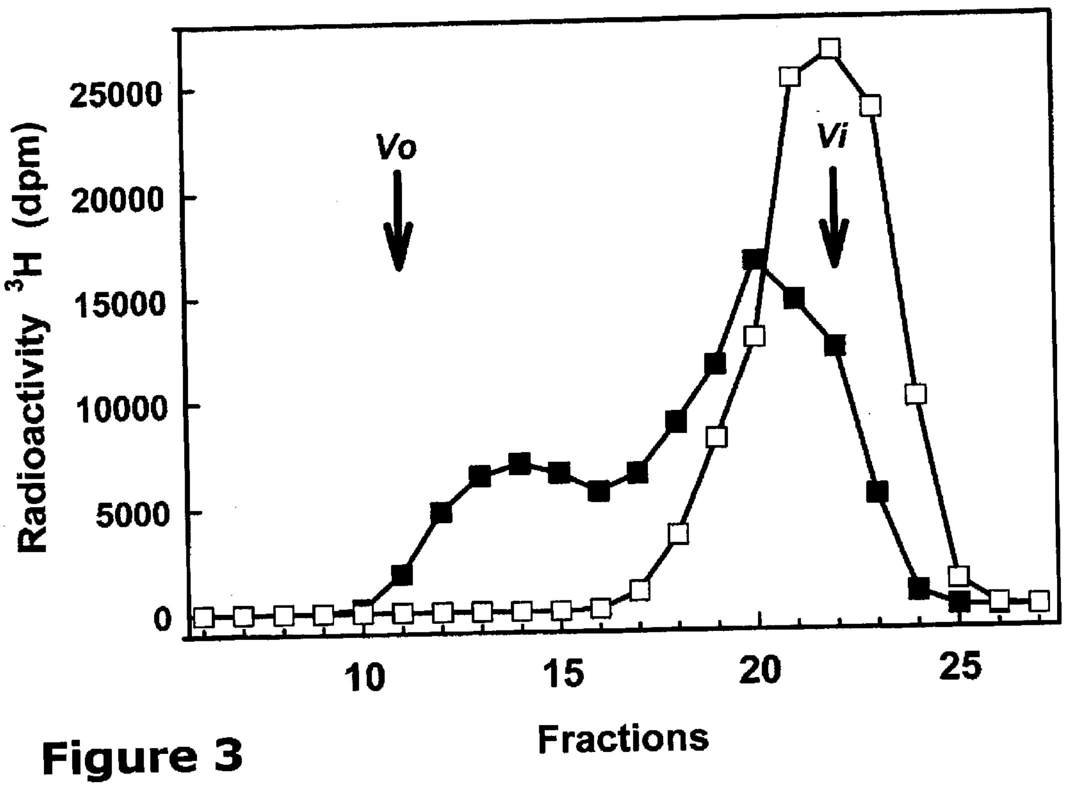
FIG. 3 is a graphical plot showing HA tetramer elongation into larger polymers by PmHAS-D.

Gel filtration chromatography analysis of reactions containing recombinant PmHAS, $^3$H-HA tetramer, UDP-GlcNAc and UDP-GlcUA show that labeled polymers from 0.5 to $5\times10^4$ Da (25–250 monosaccharides) are made as shown in FIG. 3. In FIG. 3, gel filtration analysis on Sephacryl S-200 (20 ml column, 0.7 ml fractions) shows that PmHAS-D makes HA polysaccharide using HA tetramer acceptor and UDP-sugars. Dextrans of greater than or equal to 80 kDa (~400 monosaccharides) elute in the void volume (Vo arrow). The starting tetramer elutes in the included volume (Vi arrow). Membranes (190 $\mu$g total protein), UDP-GlcUA (200 $\mu$M), UDP-GlcNAc (600 $\mu$M), and radiolabeled $^3$H-HA tetramer ($1.1\times10^5$ dpm) were incubated for 3 hours before gel filtration (solid squares). As a negative control, a parallel reaction containing all the components except for UDP-GlcNAc was analyzed (open squares). The small primer was elongated into higher molecular weight product if both precursors were supplied. In a parallel reaction without UDP-GlcNAc, the elution profile of the labeled tetramer is not altered.

The activity of the native PmHAS from *P. multocida* membranes, however, is not stimulated by the addition of HA oligosaccharides under similar conditions. The native PmHAS enzyme has an attached or bound nascent HA chain that is initiated in the bacterium priorto membrane isolation. The recombinant enzyme, on the other hand, lacks such a nascent HA chain since the *E. coli* host does not produce the UDP-GlcUA precursor needed to make HA polysaccharide. Therefore, the exogenous HA-derived oligosaccharide has access to the active site of PmHAS and can be elongated.

The tetramer from bovine testicular hyaluronidase digests of HA terminates at the nonreducing end with a GlcUA residue and this molecule served as an acceptor for HA elongation by PmHAS. On the other hand, the Δtetramer and Δhexamer oligosaccharides produced by the action of Streptomyces HA lyase did not stimulate HA polymerization as shown in FIG. 1; "unsHA4/6". As a result of the lyase eliminative cleavage, the terminal unsaturated sugar is missing the C4 hydroxyl of GlcUA which would normally be extended by the HA synthase. The lack of subsequent polymerization onto this terminal unsaturated sugar is analogous to the case of dideoxynuclcotides causing chain termination if present during DNA synthesis. A closed pyranose ring at the reducing terminus was not required by PmHAS since reduction with borohydride did not affect the HA tetramer's ability to serve as an acceptor thus allowing the use of borotritide labeling to monitor the fate of oligosaccharides.

Neither recombinant Group A HasA nor recombinant DG42 produced elongated HA-derived oligosaccharides into larger polymers in yeast. First, the addition of HA tetramer (or a series of longer oligosaccharides) did not significantly stimulate nor inhibit the incorporation of radiolabeled UDP-sugar precursors into HA (≧±5% of control value). In parallel experiments, the HAS activity of HasA or DG42 was not affected by the addition of chitin-derived oligosaccharides. Second, the recombinant enzymes did not elongate the radiolabeled HA tetramer in the presence of UDP-sugars (Table II). These same preparations of enzymes, however, were highly active in the conventional HAS assay in which radiolabeled UDP-sugars were polymerized into HA.

TABLE II

| Enzyme | Units[a] | EDTA | Incorporation of HA4 into polymer (pmoles) |
|---|---|---|---|
| PmHAS | 6[b] | − | 240 |
| | | + | 1.7 |
| HasA | 9,800 | − | ≦0.2 |
| | | + | ≦0.2 |
| DG42 | 11,500 | − | ≦0.1 |
| | | + | ≦0.3 |

[a]pmoles of GlcUA transfer/hr in the conventional HAS assay
[b]measured without HA tetramer; 360 units with 100 $\mu$M HA tetramer.

As shown in Table II, the various recombinant enzymes were tested for their ability to convert HA tetramer into molecular weight products. The reactions contained radiolabeled HA tetramer (5–$8\times10^5$ dpm), 750 $\mu$M UDP-GlcNAc, 360 $\mu$M UDP-GlcUA, 20 mM $XCl_2$, 50 mM Tris, pH 7–7.6 (the respective X cation and pH values used for each enzyme were: PmHAS, Mn/7.2; Xenopous DCG42, Mg/7.6; Group A streptococcal HasA, Mg/7.0), and enzyme (units/reaction listed). As a control, parallel reactions in which the metal ion was chelated (22 mM ethylenediaminetetraacetic acid final; EDTA column, rows with +) were tested; without free metal ion, the HAS enzymes do not catalyze polymerization. After 1 hour incubation, the reactions were terminated and subjected to descending paper chromatography. Only PmHAS-D could elongate HA tetramer even though all three membrane preparations were very active in the conventional HAS assay (incorporation of[$^{14}$C]GlcUA from UDP-GlcUA into polymer when supplied UDP-GlcNAc).

Figure 4:
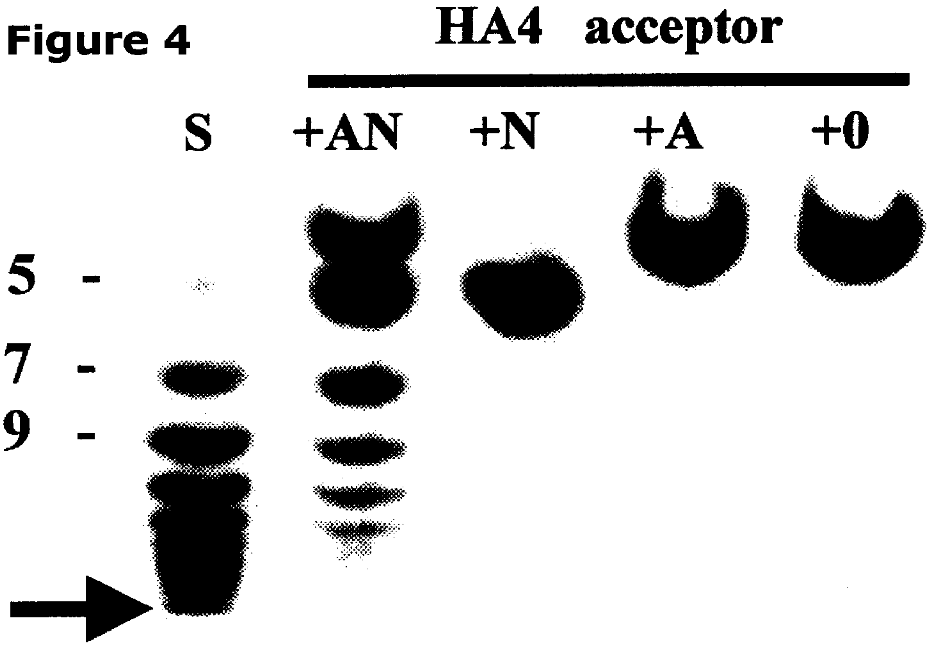
FIG. 4 is a graphical representation of a thin layer chromatography analysis of PmHAS extension of HA tetramer.

Thin layer chromatography was utilized to monitor the PmHAS-catalyzed elongation reactions containing $^3$H-labeled oligosaccharides and various combinations of UDP-sugar nucleotides. FIG. 4 demonstrates that PmHAS elongated the HA-derived tetramer by a single sugar unit if the next appropriate UDP-sugar precursor was available in the reaction mixture. GlcNAc derived from UDP-GlcNAc was added onto the GlcUA residue at the nonreducing terminus of the tetramer acceptor to form a pentamer. On the other hand, inclusion of only UDP-GlcUA did not alter the mobility of the oligosaccharide. If both HA precursors are supplied, various longer products are made. In parallel reactions, control membranes prepared from host cells with a vector plasmid did not alter the mobility of the radiolabeled HA tetramer under any circumstances. In similar analyses monitored by TLC, PmHAS did not utilize labeled chitopentaose as an acceptor.

As shown in FIG. 4, PmHAS extended an HA tetramer. In FIG. 4. radiolabeled HA tetramer (HA4 $8\times10^3$ dpm $^3$H) with a GlcUA at the nonreducing terminus was incubated with various combinations of UDP-sugars (A, 360 $\mu$M UDP-GlcUA; N, 750 $\mu$M UDP-GlcNAc; 0, no UDP-sugar), and PmHAS (55 $\mu$g membrane protein) in assay buffer for 60 minutes. The reactions (7 $\mu$l total) were terminated by heating at 95 degrees Celsius for 1 minute and clarified by centrifugation. Portions (2.5 $\mu$l) of the supernatant were spotted onto the application zone of a silica TLC plate and developed with solvent (1.25:1:1 butanol/acetic acid/water). The beginning of the analytical layer is marked by an arrow. The positions of odd-numbered HA oligosaccharides (S lane) are marked as number of monosaccharide units. This autoradiogram (4 day exposure) shows the single addition of a GlcNAc sugar onto the HA tetramer acceptor to form a pentamer when only the subsequent precursor is supplied (N). The mobility of the labeled tetramer is unchanged if only the inappropriate precursor, UDP-GlcUA (A), or no UDP-sugar (0) is present. If both UDP-sugars are supplied, then a ladder of products with sizes of 5, 7, 9, 11, and 13 sugars is formed (+AN). In a parallel experiment, chitopentaose ($8\times10^4$ dpm $^3$H) was tested as an acceptor substrate. Under no condition was this structurally related molecule extended by PmHAS.

Figure 5:
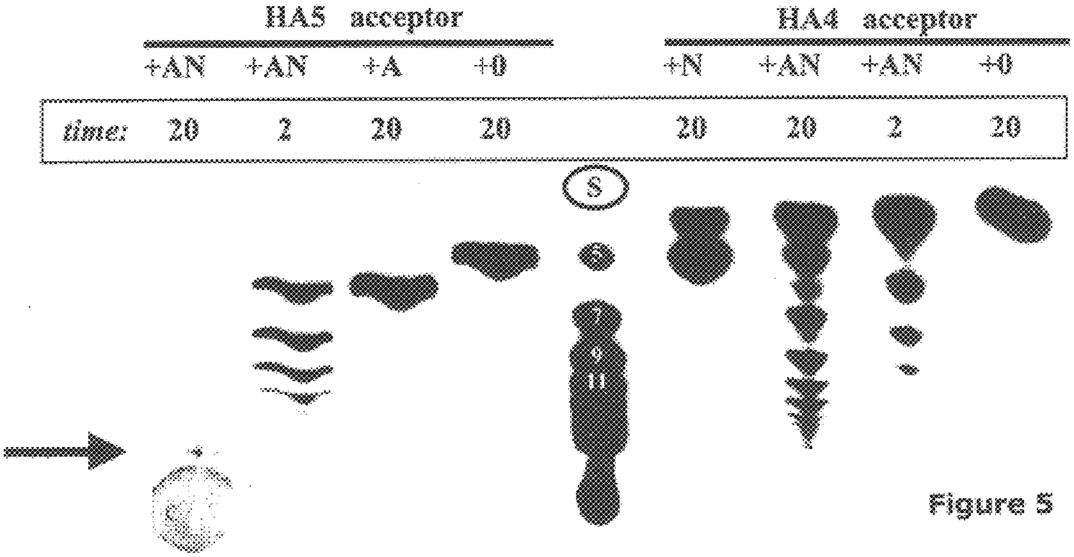
FIG. 5 is a graphical representation of thin layer chromatography analysis of the early stages of HA elongation.

HA-derived oligosaccharides with either GlcUA or GlcNAc at the nonreducing terminus served as acceptors for PmHAS (FIG. 5). In FIG. 5, radiolabeled HA pentamer (HA5, $5\times10^3$ dpm $^3$H) or HA tetramer (HA4, $25\times10^3$ dpm $^3$H) was incubated with PmHAS and various combinations of UDP-sugars (as in FIG. 4) for 2 or 20 minutes. Portions (1.5 μl) of the supernatant were spotted onto the TLC plate and developed in 1.5:1:1 solvent. This autoradiogram (1 mo. exposure) shows the single addition of a sugar onto an acceptor when only the appropriate precursor is supplied (HA4, N lane and HA5, A lane). If both UDP-sugars are supplied (+AN lanes), then a ladder of products with final sizes of 6, 8, and 10 sugars is formed from either HA4 or HA5 in 2 minutes. After 20 minutes, a range of odd- and even-numbered product sugars are observed in reactions with HA4 and both UDP-sugars. In the 20 minute reaction with HA5 and both UDP-sugars, the HA products are so large that they do not migrate from the application zone.

Within two minutes, 2 to 6 sugar units were added, and after 20 minutes, 9 to ≧15 units were added. In the experiments with the HA tetramer and both sugars, a ladder of even- and odd-numbered products is produced at the 20 minute time point. Therefore, in combination with the results of the single UDP-sugar experiments, the PmHAS enzyme transfers individual monosaccharides sequentially during a polymerization reaction.

1. HA Synthase Isolation and Assays—Membrane preparations containing recombinant PmHAS (GenBank AF036004) were isolated from *E. coil* SURE(pPmHAS). Membrane preparations containing native PmHAS were obtained from the *P. multocida* strain P-1059 (ATCC #15742). PmHAS was assayed in 50 mM Tris, pH 7.2, 20 mM $MnCl_2$, and UDP-sugars (UDP-[$^{14}$C]GlcUA, 0.3 Ci/mmol, NEN and UDP-GlcNAc) at 30° C. The reaction products were analyzed by various chromatographic methods as described below. Membrane preparations containing other recombinant HAS enzymes, Group A streptococcal HasA or Xenopus DG42 produced in the yeast *Saccharomyces cerevisiae*, were prepared.

2. Acceptor Oligosaccharides—Uronic acid was quantitated by the carbazole method. Even-numbered HA oligosaccharides [$(GlcNAc\text{-}GlcUA)_n$] were generated by degradation of HA (from Group A Streptococclus) with either bovine testicular hyaluronidase Type V (n=2–5) or *Streptomyces hyaluroniticus* HA lyase (n=2 or 3) in 30 mM sodium acetate, pH 5.2, at 30° C. overnight. The latter enzyme employs an elimination mechanism to cleave the chain resulting in an unsaturated ΔGlcUA residue at the nonreducing terminus of each fragment. For further purification and desalting, some preparations were subjected to gel filtration with P-2 resin (BioRad) in 0.2 M ammonium formate and lyophilization. Odd-numbered HA oligosaccharides [$GlcNAc(GlcUA\text{-}GlcNAc)_n$] ending in a GlcNAc residue were prepared by mercuric acetate-treatment of partial HA digests generated by HA lyase (n=2–7). The masses of the HA oligosaccharides were verified by matrix-assisted laser desorption ionization time-of-flight mass spectrometry. Sugars in water were mixed with an equal volume of 5 mg/ml 6-azo-2-thiothymine in 50% acetonitrile/0.1% trifluoroacctic acid, and rapidly air-dried on the target plate. The negative ions produced by pulsed nitrogen laser irradiation were analyzed in linear mode (20 kV acceleration; Perceptive Voyagera).

Other oligosaccharides that are structurally similar to HA were also tested in HAS assays. The structure of heparosan pentamer derived from the *E. coli* K5 capsular polysaccharide is β(1,4)GlcNAc-α(1,4)GlcUA]$_2$-β(1,4)GlcNAc; this carbohydrate has the same composition as HA but the glycosidic linkages between the monosaccharides are different. The chitin-derived oligosaccharides. chitotetraose and chitopentaose, are β(1,4)GlcNAc polymers made of 4 or 5 monosaccharides, respectively.

Various oligosaccharides were radiolabeled by reduction with 4 to 6 equivalents of sodium borotritide (20 mM, NEN; 0.2 Ci/mmol) in 15 mM NaOH at 30° C. for 2 hrs. $^3$H-oligosaccharides were desalted on a P-2 column in 0.2 M ammonium formate to remove unincorporated tritium and lyophilized. Some labeled oligosaccharides were further purified preparatively by paper chromatography with Whatman 1 developed in pyridine/ethyl acetate/acetic acid/$H_2O$ (5:5:1:3) before use as an acceptor.

3. Chromatographic Analyses of HA Synthase Reaction Products—Paper chromatography with Whatman 3M developed in ethanol/1M ammonium acetate, pH 5.5 (65:35) was used to separate high molecular weight HA product (which remains at the origin) from UDP-sugars and small acceptor oligosaccharidcs. In the conventional HAS assay, radioactive UDP-sugars are polymerized into HA. To obtain the size distribution of the HA polymerization products, some samples were also separated by gel filtration chromatography with Sephacryl S-200 (Pharmacia) columns in 0.2 M NaCl, 5 mM Tris, pH 8. Columns were calibrated with dextran standards. The identity of the polymer products was assessed by sensitivity to specific HA lyase and the requirement for the simultaneous presence of both UDP-sugar precursors during the reaction. Thin layer chromatography [TLC] on high performance silica plates with application zones (Whatman) utilizing butanol/acetic acid/water (1.5:1:1 or 1.25:1:1) development solvent separated $^3$H-labeled oligosaccharides in reaction mixes. Radioactive molecules were visualized after impregnation with EnHance spray (NEN) and fluorography at −80° C.

An anti-PmHAS monospecific antibody reagent has also been identified that routinely monitors the protein by Western blots or immunoassays; this reagent can be used to normalize protein expression levels. The DNA inserts encoding the enzyme sequence from interesting mutants picked up in screens can be subcloned and completely sequenced to verify and to identify the mutation site.

A series of truncated versions of PmHAS (normally a 972-residue membrane protein) were, created which produce proteins with altered physical properties (i.e. proteins that are more conducive to high-level expression and purification) and altered function (i.e. single transferase activity). Polymerase chain reaction [PCR] was used to amplify a portion of the PmHAS gene using a primer corresponding to the authentic N-terminus sequence and a primer corresponding to an internal coding region which ended in a stop codon. The coding regions for the truncated proteins were cloned into an *Escherichia coli* expression plasmid (pKK223-3; Pharmacia) under control of the tac promoter. The DNA sequence was verified by automated sequencing.

The truncation series was generated and tested for activity. All proteins were made at the expected molecular weight, but not all proteins were active.

TABLE III

| Name | Residues of PmHAS | Activity |
|---|---|---|
| PmHAS-A | 437–972 | N.D. |
| PmHAS-B | 437–756 | N.D. |
| PmHAS-C | 1–756 | HA Synthase |
| PmHAS-D | 1–703 | HA Synthase |
| PmHAS-E | 1–650 | GlcNAc Transferase |
| PmHAS-F | 152–756 | N.D. |

N.D.-no activity detected.

Figure 6:
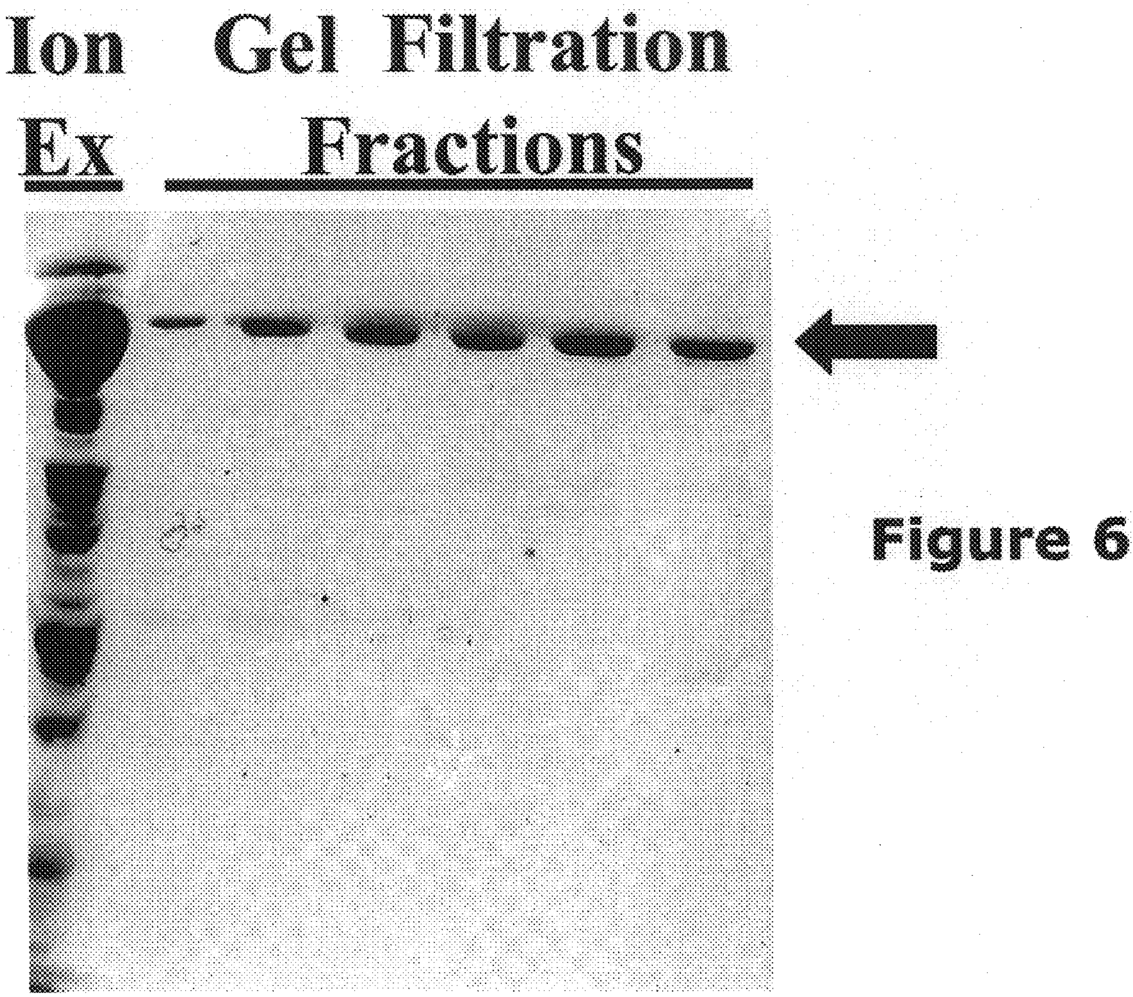
FIG. 6 is an electrophoresis gel showing the purification of PmHAS-D.

Analysis of induced cell cultures containing the plasmid with a 703-residue open reading frame revealed that a new 80-kDa protein, named PmHAS-D, was produced in large quantities. Furthermore, functional PmHAS-D was present in the soluble fraction of the cell lysate; thus allowing for rapid extraction and assay of the enzyme. PmHAS-D was purified by sequential chromatography steps shown in FIG. 6. In FIG. 6, a soluble, active form of the HA synthase was constructed with molecular biological techniques. The recombinant enzyme from *E. Coli* was purified by conventional chromatography with yields of up to 20 mg/liter of cell culture. FIG. 6 is a stained electrophoretic gel loaded with samples of PmHAS-D (marked with a star) during different stages of chromatography. This catalyst (and improved mutant versions) can be used to prepare HA coatings on artificial surfaces or HA extensions on suitable acceptor molecules.

The PmHAS-D is highly active and at least 95% pure as assessed by denaturing polyacrylamide gel electrophoresis. Mass spectrometric analysis indicates that the PmHAS-D is the desired protein due to the close agreement of the calculated and the observed mass values. A buffer system has also been developed to stabilize the enzymatic activity in the range of 0° to 37° C.

Site-directed mutagenesis was then used to prepare versions of PmHAS-D with altered enzymatic activity. Synthetic DNA oligonucleotides and multiple rounds of extension with Pfu DNA polymerase were used to add mutations to the coding region using the Quick-Change system from Stratagene. Through use of primers with mixed bases at certain positions, a wide variety of amino acid changes were generated. DNA sequencing was then employed to identify the changed residue. Several PmHAS-D mutants have also been obtained having altered sugar transferase activity. Similar methodology has also been used to alter the HA-acceptor binding site of PmHAS-D.

Two positions of the PmHAS-D sequence were mutated in the initial trials. Conserved aspartates at residue 196 or 477 were critical for HAS activity.

TABLE IV

| Mutation (*) | HAS Activity | GlcNActase | GlcUAtase |
|---|---|---|---|
| D196E | W/O | W/O | YES |
| D196N | W/O | W/O | YES |
| D196K | W/O | W/O | YES |
| D477E | W/O | YES | W/O |
| D477N | W/O | YES | W/O |
| D477K | W/O | YES | W/O |
| WILD TYPE CONTROL | YES | YES | YES |

(*) Single letter code for amino acid changes at position 196 or 477 (as noted) in which type aspartate (D) is exchanged with an asparagine (N), glutamate (E), or lysine (K).
"W/O" weak (<8% of wild-type) or no activity.

Figure 7:
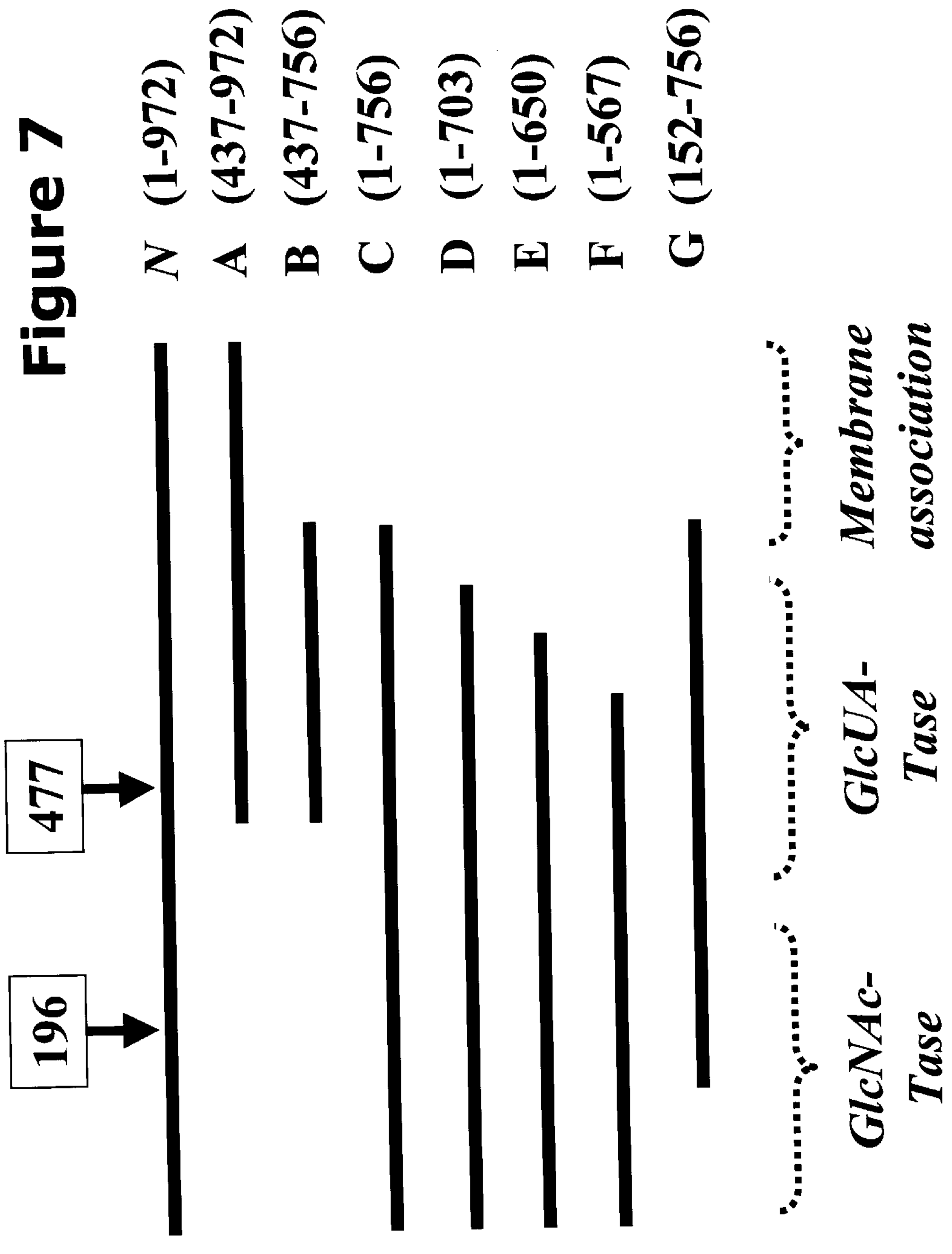
FIG. 7 is a pictorial representation of the PmHAS-D mutants.

The mutant enzymes are useful for adding on a single GlcNAc or a single GlcUA onto the appropriate acceptor oligosaccharide. It appears that PmHAS has two domains or two modules for transferring each sugar. One of ordinary skill in the art. given this specification, would be able to shift or to combine various domains to create new polysaccharide synthases capable of producing new polysaccharides with altered structures. Within such use. a variety of grafting techniques arise which utilize PmHAS as the prototype. A graphical representation of each mutant as it relates to the PmHAS-D sequence, is shown in FIG. 7.

Figure 8:
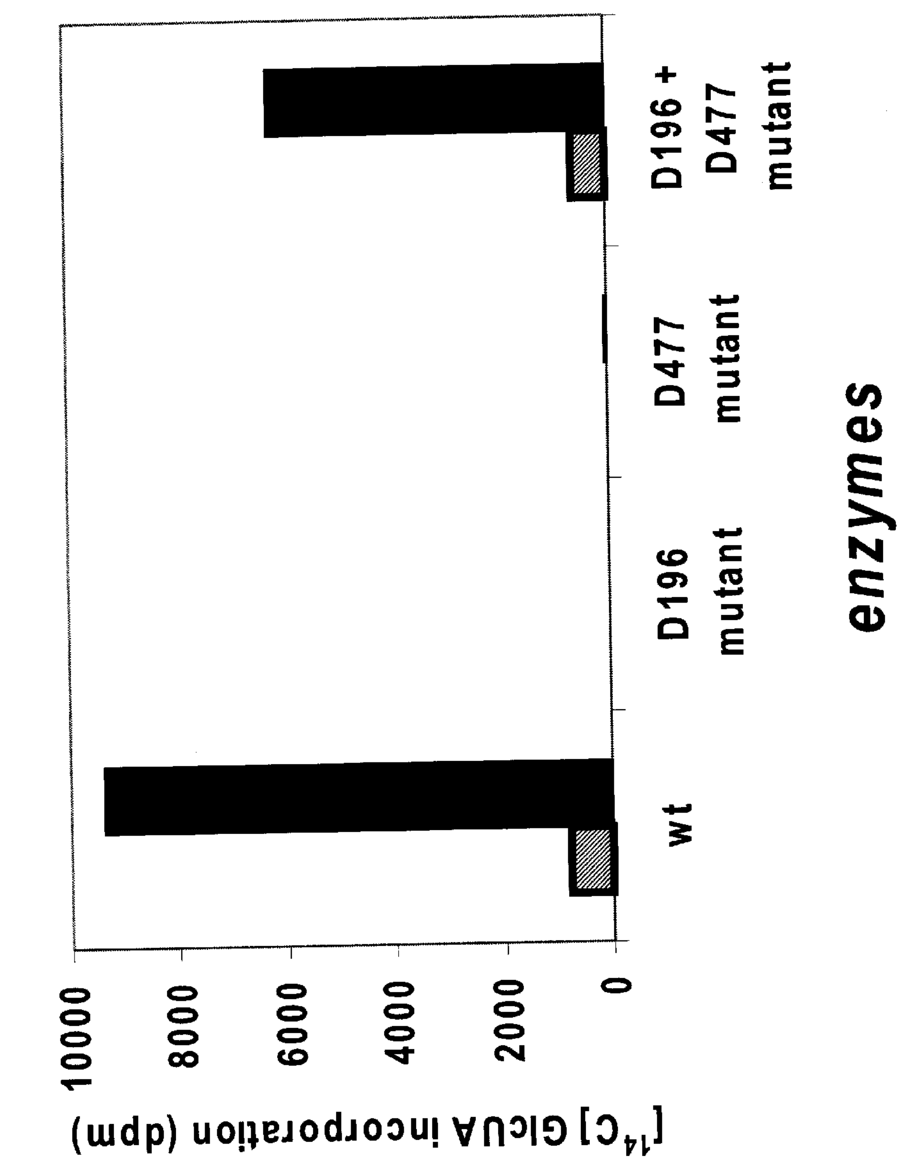
FIG. 8 is a graphical representation of a mutant combination assay.

FIG. 8 is a graphical representation of a mutant combination assay. HAS enzyme assays were performed in the presence of wild type PmHAS alone, D196 mutant alone, D477 mutant alone, or in the presence of both D196 and D477 mutants. Equal amounts of each enzyme were tested with a small amount of HA acceptor sugar in the typical reaction buffer at 30 degrees Celsius. Two time points were measured (cross-hatched, 25 minutes; black, 1.5 hours) for each assay. The two mutants work together to make HA polymer; by itself, a single mutant cannot make HA polymer.

Enzyme activity of the PmHAS-D mutants is shown in FIG. 9. Extracts of the mutants were used for all three kinds of assays: for HA polymer production. for GlcUA-Tase activity and for GlcNAc-Tase activity. Equivalent amounts of PmHAS-D proteins (based on Western blot analysis) were assayed. The activities were indicated as the percentage of the activity of wild type PmHAS-D.

With the advent of new biomaterials and biomimetics, hybrid polysaccharide materials will be required to serve the medical field. A major goal of bioengineering is the design of implanted artificial devices to repair or to monitor the human body. Versatile semiconductors, high-strength polymers, and durable alloys have many properties that make these materials desirable for bioengineering tasks. However, the human body has a wide range of defenses and responses that hinder the utilization of modern man-made substances. As different tissues and organs are identified as future recipients of biotechnology, it will be imperative to have an assortment of non-immunogenic polymers that can act as adhesives or protective coatings. Emulsification or adhesion industrial processes are also well suited for use with the present invention and other more suitable enzymes may be employed to graft useful molecules.

Chemical sensors which utilize electrochemical reactions have promise in many biomedical applications. In particular, the measurement of blood glucose for home monitoring of diabetics is of great interest. Unfortunately, biochemical sensors for glucose and other biological chemicals have not achieved their anticipated level of success. Problems with sensor reliability, selectivity, and material stability have delayed the fruition of the biosensor market. New methods to deposit selective materials onto electronic substrates while maintaining compatibility with biological systems are needed. The present invention provides such a method. Through the use of the PmHAS-D enzyme, an electronic or metallic substrate which has been primed with a suitable exogenous HA oligosaccharide can be coated with a layer of HA. Such a layer of HA would protect the electronic substrate from the biological immune systems while allowing full function of the electronic or metallic material.

Presently, commercially available glucose sensors operate through the electrochemical oxidation and reduction of glucose oxidase found in a patient's blood. Typically the patient must prick their finger several times daily to obtain the blood sample needed for the sensor. Once in the sensor, the glucose oxidase reacts with glucose to form gluconic acid. The reduced form of the enzyme reacts with an electron mediator such as ferricyanide to form ferrocyanide. A sensor electrode oxidizes the ferrocyanide creating a current proportional to the concentration of glucose is in the blood.

As with many biosensors, a significant shift toward continual monitoring using minimally invasive or implantable sensing devices, which require fully integrated microelectronic capabilities while maintaining biocompatibility, remains a future trend in glucose sensor development. A glucose microsensor using microfabrication of sensor arrays is a convenient means of implantation and has a high sensitivity threshold. Presently, no commercial glucose microsensor exists. Issues such as sensor selectivity and stability have hindered the development of an implantable glucose microsensor. Because of the harsh environment of the human body, biocompatibility becomes an important issue to the stability and reliability of the biosensor. Those working in the art have looked at a variety of polymer membranes that protect the sensor from the body. Some have also chemically attached electron mediators and enzymes directly to polymer materials thereby providing electrical connection and improved stability and safety of the sensor for in vivo use. A means of incorporating biological materials to the sensing surface while maintaining sensing function would be beneficial. The present invention provides such a method for producing non-immunogenic coating for sensors as well as other biomaterials.

In the present invention, HA oligosaccharides and other novel primer materials are deposited onto the inorganic substrate using chemistry known to those of ordinary skill in the art and similar reaction processes. For example, a reactive epoxy surface can be made which in turn can react with amino compounds derived from HA-oligosaccharides. Once the primer materials have been deposited onto the inorganic substrate, PmHAS-D is utilized to form a protective coating of HA-polymer on the inorganic substrate. The HA polymer coating thereby protects the substrate from the body's immune system while allowing the substrate to perform an indicated purpose such as sensing, detection or drug delivery.

The majority of existing artificial materials suitable for implants and sensors, to some degree, usually (a) cause a foreign-body reaction due to the interactions with tissues or biological fluids or (b) lack substantial connectivity with the body due to their relative inertness. The HA polymer coating of the present invention overcomes these two stumbling blocks. A uniform coating of naturally occurring HA prevents an artificial components implanted into the body from spawning adverse effects such as an immune response, inappropriate clotting and/or inflammation. Furthermore, because HA is involved in maintaining the integrity of tissues and wound-healing, the HA polysaccharide coating encourages the acceptance of the artificial structure within the body.

The HA polymer attached to a biosensor acts as an external barrier protecting the sensor from the body's environment. However, in any sensing application, the chemical analyte must be able to contact the sensing material. Therefore, the HA polymer layer must allow transport of glucose to regions inside the sensor. Other molecules also exist in the blood that may interfere with the sensor response. Phase equilibrium between components in the blood and the HA polymer layer determine the local environment of the sensing layer. The transport properties of thin HA polymer layers also allow for the use of the HA polymer as a packaging material. The HA polymer outer coating allows transport of the glucose analyte in a diffusion-controlled manner while-preventing biological materials from damaging the electronic device. As the HA polymer to be deposited consists of tangled, linear chains of hydrophilic sugars, glucose and other small compounds move relatively freely in the layer. On the other hand, medium to large proteins, which may foul the sensor, are excluded from the HA layer.

Figure 10:
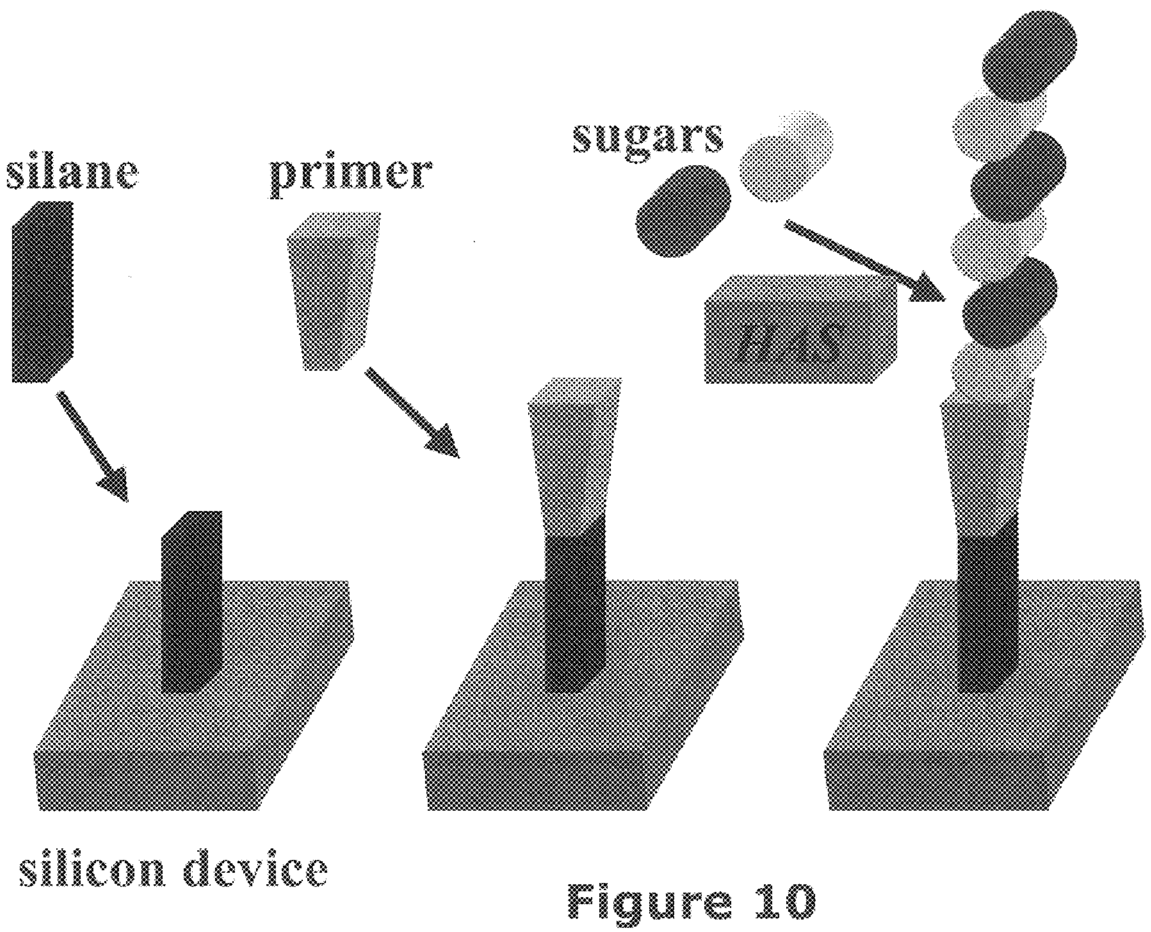
FIG. 10 is a schematic representation of first generation of HA coating on silicon.

As stated previously, there is precedent for utilizing HA in the medical treatment of humans. Currently, HA is employed in eye surgery, joint fluid replacement, and some surgical aids. Much investigation on the use of HA to coat biomedical devices is also underway. In the previously described coating methods, HA extracted from animal or bacterial sources is typically chemically crosslinked or physically adsorbed onto a surface. Potential problems with these methodologies include: (a) immunoreaction with animal-borne contaminants and/or introduced chemical crosslinking groups and (b) the lack of reproducibility of the coating configuration. In the present invention, HA polymer chains are produced in situ using the purified biosynthetic enzyme, PmHAS-D. (FIG. 10). In FIG. 10, the schematic representation of 1$^{st}$ generation HA coating on silicon is shown. A silane and then a sugar primer are attached to the silicon surface. PmHAS-D then elongates the primer with appropriate sugars to form a biocompatible coating. The length of the HA polymer (100 to $10^3$ sugars) are adjusted to fit the particular coating application.

Due to the relative absence of foreign components or artificial moieties, no immunological problems occur. Depending on the particular application, the polymer length and the chain orientation can be controlled with precision. The polysaccharide surface coatings of the present invention improves the biocompatibility of the artificial material, lengthens the lifetime of the device in the cellular environment, and encourages natural interactions with host tissues.

With regard to surface coatings on solid materials, polyacrylamide beads have been coated with the HA polymer using PmHAS-D as the catalyst. First, aminoethyl-beads were chemically primed with HA oligosaccharide (a mixture of 4, 6, and 8 sugars long) by reductive amination. Beads, HA oligosaccharide, and 70 mM $NaCNBH_4$ in 0.2 M borate buffer, pH 9, were incubated at 42° C. for 2 days. The beads were washed with high and low salt buffers before use in the next step. Control beads without priming sugar or with chitopentaose [$(GlcNAc)_5$] were also prepared; beads without HA would not be expected to prime HA synthesis and the chitopentaose does not serve as an acceptor for PmHAS. Second, the various preparations of beads (15$\mu$ liters) were incubated with PmHAS-D (3 $\mu$g), 150 mM UDP-[$^3$H]GlcNAc, 60 mM UDP-[$^{14}$C]GlcUA, 20 mM $MnCl_2$, in 50 mM Tris. pH 7.2, at 30° C. for 60 min. The beads were then washed with high and low salt buffers. Radioactivity linked to beads (corresponding to the sugars) was then measured by liquid scintillation counting Table V.

TABLE V

| Bead Type | Enzyme Added? | Bound GlcUA ($^{14}$C dpm) | Bound GlcNAc ($^3$H dpm) |
|---|---|---|---|
| HA primer | yes | 990 | 1140 |
| HA primer | no | 10 | 10 |
| Chito primer | yes | 24 | 18 |
| No primer | yes | 5 | 35 |

Only HA beads primed with the HA oligosaccharide and incubated with PmHAS-D incorporated the radiolabel from both UDP-sugar precursors indicating that the short HA sugar attached to the bead was elongated into a longer HA polymer by the enzyme. Thus far, no other known HA synthase possesses the desired catalytic activity to apply an HA polymer coating onto a primed substrate.

Thus, as shown above, an authentic HA oligosaccharide primer was chemically coupled to a polyacrylamide surface and then this primer was further elongated using the PmHAS enzyme and UDP-sugars. Depending on the substrate, the reaction conditions can be optimized by one of ordinary skill in the art. For example, the mode of semiconductor modification, buffer conditions, HA elongation reaction time, and stoichiometry can be varied to take into account any single or multiple reaction variation. The resulting coatings can then be evaluated for efficacy and use.

In order to scale-up and to facilitate the biocompatible HA coating process to a level practical for medical devices in the future, (a) a new synthetic molecule that would substitute for the HA oligosaccharide with the original PmHAS-D enzyme will be used; or (b) a mutant form of the PmHAS-D enzyme that will utilize a "simpler" organic molecule as the primer will be used.

The critical structural elements of the HA oligosaccharide acceptor or primer molecule are currently being tested and identified. The smallest acceptor molecule with activity tested thus far is an HA tetramer [non-reducing-GlcUA-GlcNAc-GlcUA-GlcNAc-reducing]. Recent data suggests that the PmHAS-D enzyme has some flexibility with respect to the identity of the hexosamine group; i.e. other isomers will substitute for the GlcNAc sugar. For example, chondroitan pentamer [GalNAc-GlcUA-GalNAc-GlcUA-GalNAc], serves as an effective acceptor for recombinant PmHAS. Therefore, a synthetic molecule consisting of several hydroxyl groups, a pair of negatively charged groups (corresponding to the carboxyl groups of GlcUA sugar), and hydrophobic patches (analog of the carbon-rich side of the sugar ring) may work as a primer. Such an approach is not unprecedented as the polymerization of heparin, a glycosaminoglycan, can be primed with a rather simple aromatic xyloside instead of a complex proteoglycan core.

Computer modeling of HA oligosaccharides can visualize potential molecular shape. However, some proteins distort the sugar chains upon binding, thus making computer modeling somewhat more complicated. The most efficacious method of finding an artificial primer is a combinatorial chemistry approach. Closely related series of molecules are screened by high-throughput assay methodologies in order to detect HA elongation. Native PmHAS-D is then tested for the ability to add an HA polymer onto synthetic primer candidates in a typical 96-well plate format. For example, a series of synthetic peptides (6 to 8 residues) terminating with a GlcNAc group using conventional $F^{moc}$ chemistry can be generated. Such peptides are particularly promising because they can adopt a variety of conformations and fit within the PmHAS-D HA-binding pocket via an induced fit mechanism. Synthetic peptide chemistry is also much less cumbersome than carbohydrate chemistry. One of ordinary skill in the art, given the present specification, would be capable of using the known synthetic peptide chemistry techniques.

The amino acids are chosen with the goal of mimicking the properties of the GlcNAcGlcUA sugar repeats of HA. For example, use of glutamate or asparatate as a substitute for the acid group of GlcUA, or use of glutamine or asparagine as a substitute for the amide group of GlcNAc. Serine, threonine, or tyrosine can be used as substitutes for the hydroxyl groups and sugar rings in general. The peptide library terminates with a GlcNAc sugar group so that the demands on the PmHAS-D enzyme's binding site and catalytic center are not overly burdensome. A vast variety of distinct peptides are made in parallel with a combinatorial approach; for example, with a hypothetical 6–7 residue peptide containing 1 to 3 different amino acids at each position, there are hundreds of possible peptides. The peptide combinatorial libraries will either be immobilized on plastic pins or plates.

The present invention also encompasses the development of a mutant version of PmHAS-D that will utilize a simpler molecule than an HA oligosaccharide as a primer. Chitopentaose (β1,4-GlcNAc homopolymer) is one such potential variant primer. Native PmHAS-D does not utilize chitopentaose as a primer, but a mutant PmHAS-D may potentially elongate chitopentaose, a more readily available substance. The chitopentaose primer is attached to the solid phase by reductive amination to an amino-containing plate or to a carrier protein (albumin) for immobilization on a normal plastic plate. Various mutants could then be screened for function. Other potential non-sugar mimics contemplated for use are short poly(ethleneglycol)-based copolymers containing styrene, sulfonate, acrylate, and/or benzoate groups.

Photoaffinity labeling is used to cross-link a radioactive HA oligosaccharide analog containing an aryl azide to the PmHAS-D protein. The binding site of the PmHAS-D protein is obtained through peptide mapping and Edman sequencing. With this information, mutants are prepared with alterations at the binding site. In the chitopentaose example, removal of some of the basic residues of the HA-binding site (which normally contact the carboxylate of GlcUA) and substitution of neutral polar residues would be chosen. As described above, a variety of site-directed mutants using a mutagenic oligonucleotide with mixed bases at certain positions have been generated. Such a mixed-base approach economizes on the number of custom oligonucleotides and transformations required. A high-throughput screen is then used to assess the ability of the mutant PmHASs to elongate the synthetic primer with a HA chain. An empirical approach can also be used randomly mutate PmHAS (either chemical mutagens or with a passage through a mutator strain) and then screen.

Figure 11:
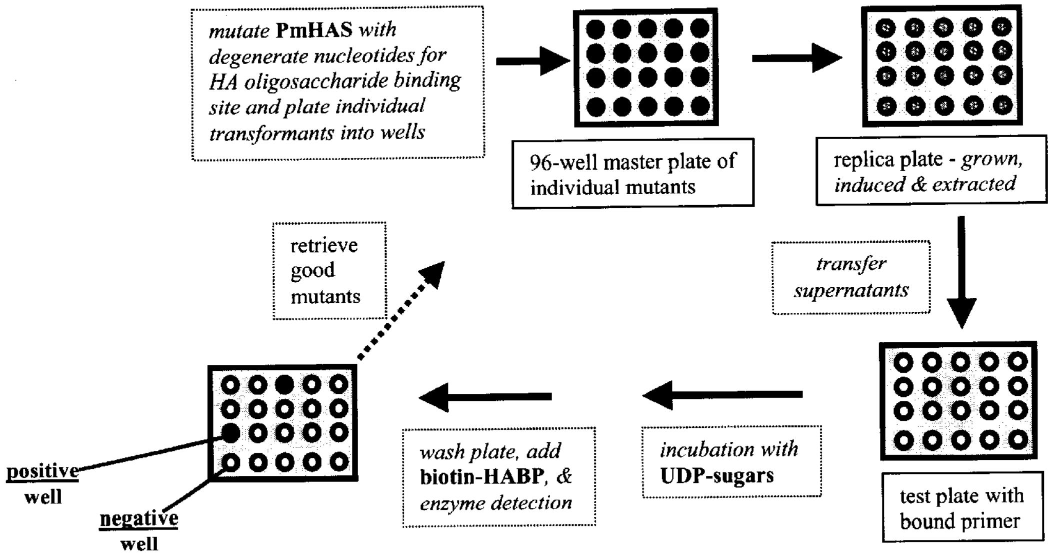
FIG. 11 is a graphical representation of a high-throughput assay for PmHAS-D mutants.

An assay has been designed to measure successful HA elongation reactions in a 96-well format (FIG. 11). The assay is shown in FIG. 11 in a graphical representation. Utilizing this assay many mutants can be screened in parallel. This screening method is facilitated by the fact that (i) a protocol to readily extract functional recombinant PmHAS-D from *E. coli* cultures in a 96-well plate format with minimal processing exists and (ii) sensitive methods to detect HA on solid-phase microtiter plates exists. Cultures and extracts are transferred in parallel with multi-channel pipettes. HAS activity produced by 10–30 μl of induced cell culture (with an absorbance=1 at 600 nm) is routinely detected and the wells have a working volume of 200–300 μl, thus multiple assays or detection of low HA production is possible. Other components in the cell lysate do not interfere with the HAS assay. The extracts are stable at −80° C. for long-time storage. For detection of HA elongation, specificity of a HA-binding protein probe [HABP], biotinylated aggrecan, is capitalized upon. This probe binds elongated H-IA chains with high affinity but not small HA primers (4–6 sugars long). The bound HABP probe is detected by virtue of the biotin tag that is measured with fluorescent, radiolabeled, or enzyme-conjugated avidin (a biotin-binding protein).

In order to identify enzymes with low activities or reactions with poor primers, radioactive sugar incorporation (from UDP-[$^3$H-]GlcNAC or UDP-[$^{14}$C]GlcUA) is measured instead of using the HABP probe. Of course, the majority of mutants and primers will not possess desirable characteristics, but the high-throughput screen allows those rare target molecules that facilitate the HA-coating process to be easily identified.

Biomaterials also play a pivotal role in the field of tissue engineering. Biomimetic synthetic polymers have been created to elicit specific cellular functions and to direct cell-cell interactions both in implants that are initially cell-free, which may serve as matrices to conduct tissue regeneration, and in implants to support cell transplantation. Biomimetic approaches have been based on polymers endowed with bioadhesive receptor-binding peptides and mono- and oligosaccharides. These materials have been patterned in two- and three-dimensions to generate model multicellular tissue architectures, and this approach may be useful in future efforts to generate complex organizations of multiple cell types. Natural polymers have also played an important role in these efforts, and recombinant polymers that combine the beneficial aspects of natural polymers with many of the desirable features of synthetic polymers have been designed and produced. Biomaterials have been employed to conduct and accelerate otherwise naturally occurring phenomena, such as tissue regeneration in wound healing in the otherwise healthy subject; to induce cellular responses that might not be normally present, such as healing in a diseased subject or the generation of a new vascular bed to receive a subsequent cell transplant; and to block natural phenomena, such as the immune rejection of cell transplants from other species or the transmission of growth factor signals that stimulate scar formation.

Approximately 10 years ago, the concept of bioadhesion was introduced into the pharmaceutical literature and has since stimulated much research and development both in academia and in industry. The first generation of bioadhesive drug delivery systems (BBDS) were based on so-called mucoadhesive polymers, i.e. natural or synthetic macromolecules, often already well accepted and used as pharmaceutical excipients for other purposes, which show the remarkable ability to 'stick' to humid or wet mucosal tissue surfaces. While these novel dosage forms were mainly expected to allow for a possible prolongation, better localization or intensified contact to mucosal tissue surfaces, it had to be realized that these goals were often not so easily accomplished, at least not by means of such relatively straightforward technology. However, although not always convincing as a "glue", some of the mucoadhesive polymers were found to display other, possibly even more important biological activities, namely to inhibit proteolytic enzymes and/or to modulate the permeability of usually tight epithelial tissue barriers. Such features were found to be particularly useful in the context of peptide and protein drug delivery.

The primary goal of bioadhesive controlled drug delivery is to localize a delivery device within the body to enhance the drug absorption process in a site-specific manner. Bioadhesion is affected by the synergistic action of the biological environment, the properties of the polymeric controlled release device, and the presence of the drug itself. The delivery site and the device design are dictated by the drug's molecular structure and its pharmacological behavior.

One such bioadhesive known in the art is a fibrin "glue" and compositions which include one or more types of fibrin glue in combination with a medicament have been studied. For example, in order to test the effect on the handling properties of a two component fibrin glue, the viscosity of the fibrin glue was increased with sodium hyaluronate and the glue was applied to a microvascular anastomosis in rats. The femoral artery of each rat was anastomosed with three conventional sutures and then sealed with the fibrin glue. Three glues. with different viscosities were tested: original Tisseel fibrin glue (Immuno AG. Vienna); Tisseel with 0.9% sodium chloride added to the. fibrinogen component; and Tisseel with a high molecular weight sodium hyaluronate (10 mg/ml, Hcalon, Pharmacia, Sweden) added to the fibrinogen component. The increased viscosity of the fibrin glue to which hyaluronate had been added resulted in a significantly higher patency rate 20 minutes after completion of the anastomosis ($p<0.01$), and reduced the amount of fibrin that entered the vessels. Wadstrom et al. "Fibrin glue (Tisseel) added with sodium hyaluronate in microvascular anastomosing." *Scand J Plast Reconstr Surg Hand Surg* 1993 Dec;27(4)257–61.

The typical properties of the bioadhesive fibrin system described above ensue from its physiological properties. Filling the wound enhances natural biological processes of healing. The tissue reaction to the applied tissue fibrin coagulum is favorable. The treated parenchymatous organs, liver and spleen, heal with a smooth scar. The number of adhesions in the peritoneal cavity in all known treated experimental animals after treatment of the spleen was similar. Fewer adhesions are also observed when using a bioadhesive for repairing liver injuries in rabbits. The macroscopic appearance of the scar was similar, the scar was less visible in the liver parenchyma. The histological appearance was similar. The bioadhesive did not damage the tissue surrounding the parenchyma and did not act as a foreign body. These results confirm the biocompatibility of the fibrin glue as well as tissue tolerance and satisfactory healing without a reaction to the bioadhesive. After healing the bioadhesive is typically replaced by natural fibrous tissue.

Despite the effectiveness and successful use of the fibrin glue by medical practitioners in Europe, neither fibrin glue nor its essential component fibrinogen is widely used in the United States at the present time because of the general risks and problems of infection from pooled blood products contaminated with lipid-enveloped viruses such as HIV, associated with AIDS. and the hepatitis causing viruses such as HBV and HCV, as well as cytomegalovirus (CMV), Epstein-Barr virus, and the herpes simplex viruses in fibrinogen preparations. Thus, a naturally occurring or recombinantly produced bioadhesive which is not derived from pooled blood sources is actively being sought. The bioadhesive of the present invention fulfills such a need.

For example, one embodiment of the present invention is the use of sutures or bandages with HA-chains grafted on the surface or throughout the material in combination with the fibrinogen glue. The immobilized HA does not diffuse away as in current formulations, but rather remains at the wound site to enhance and stimulate healing.

Organic materials have also been postulated for use as bioadhesives. Bioadhesive lattices of water-swollen poly (acrylic acid) nano-and microparticles have been synthesized using an inverse (W/O) emulsion polymerization method. They are stabilized by a co-emulsifier system consisting of SpanTM 80 and TweenTM 80 dispersed in aliphatic hydrocarbons. The initial polymerization medium contains emulsion droplets and inverse micelles which solubilize a part of the monomer solution. The polymerization is then initiated by free radicals, and particle dispersions with a narrow size distribution are obtained. The particle size is dependent on the type of radical initiator used. With water-soluble initiators, for example ammonium persulfate, microparticles are obtained in the size range of 1 to 10 micrometer, indicating that these microparticles originate from the emulsion droplets since the droplet sizes of the W/O emulsion show similar distribution. When lipophilic radical initiators, such as azobis-isobutyronitrile, are used, almost exclusively nanoparticles are generated with diameters in the range of 80 to 150 nm, due to the limited solubility of oligomeric poly(acrylic acid) chains in the lipophilic continuous phase. These poly(acrylic acid) micro- and nanoparticles yielded excellent bioadhesive properties in an in-vitro assay and may, therefore, be suitable for the encapsulation of peptides and other hydrophilic drugs.

In the present invention, HA or chondroitin chains would be the natural substitute for poly(acrylic-acid) based materials. HA is a negatively-charged polymer as is poly(acrylic-acid), but HA is a naturally occurring molecule in the vertebrate body and would not invoke an immune response like a poly(acrylic-acid) material.

The interest in realizing 'true' bioadhesion continues: instead of mucoadhesive polymers, plant or bacterial lectins, i.e. adhesion molecules which specifically bind to sugar moieties of the epithelial cell membrane, are now widely being investigated as drug delivery adjuvants. These second-generation bioadhesives not only provide for cellular binding, but also for subsequent endo- and transcytosis. This makes the novel, specifically bioadhesive molecules particularly interesting for the controlled delivery of DNA/RNA molecules in the context of antisense or gene therapy.

For the efficient delivery of peptides, proteins, and other biopharmaceuticals by nonparenteral routes, in particular via the gastrointestinal, or GI, tract, novel concepts are needed to overcome significant enzymatic and diffusional barriers. In this context, bioadhesion technologies offer some new perspectives. The original idea of oral bioadhesive drug delivery systems was to prolong and/or to intensify the contact between controlled-release dosage forms and the stomach or gut mucosa. However, the results obtained during the past decade using existing pharmaceutical polymers for such purposes were rather disappointing. The encountered difficulties were mainly related to the physiological peculiarities of GI mucus. Nevertheless, research in this area has also shed new light on the potential of mucoadhesive polymers. First, one important class of mucoadhesive polymers, poly(acrylic acid), could be identified as a potent inhibitor of proteolytic enzymes. Second, there is increasing evidence that the interaction between various types of bio (muco)adhesive polymers and epithelial cells has direct influence on the permeability of mucosal epithelia. Rather than being just adhesives, mucoadhesive polymers may therefore be considered as a novel class of multifunctional macromolecules with a number of desirable properties for their use as biologically active drug delivery adjuvants.

In the present invention, HA or other glycosaminoglycan polysaccharides are used. As HA is known to interact with numerous proteins (i.e. RHAMM, CD44) found throughout the healthy and diseased body, then naturally occurring adhesive interactions can be utilized to effect targeting, stabilization, or other pharmacological parameters. Similarly, chondroitin interacts with a different subset of proteins (i.e. platelet factor 4, thrombin); it is likely that this polymer will yield properties distinct from HA and widen the horizon of this technology.

In order to overcome the problems related to GI mucus and to allow longer lasting fixation within the GI lumen, bioadhesion probably may be better achieved using specific bioadhesive molecules. Ideally, these bind to surface structures of the epithelial cells themselves rather than to mucus by receptor-ligand-like interactions. Such compounds possibly can be found in the future among plant lectins. novel synthetic polymers, and bacterial or viral adhesion/invasion factors. Apart from the plain fixation of drug carriers within the GI lumen, direct bioadhesive contact to the apical cell membrane possibly can be used to induce active transport processes by membrane-derived vesicles (endo- and transcytosis). The nonspecific interaction between epithelia and some mucoadhesive polymers induces a temporary loosening of the tight intercellularjunctions, which is suitable for the rapid absorption of smaller peptide drugs along the paracellular pathway. In contrast, specific endo- and transcytosis may ultimately allow the selectively enhanced transport of very large bioactive molecules (polypeptides, polysaccharides, or polynucleotides) or drug carriers across tight clusters of polarized epi- or endothelial cells, whereas the formidable barrier function of such tissues against all other solutes remains intact.

Bioadhesive systems are presently playing a major role in the medical and biological fields because of their ability to maintain a dosage form at a precise body-site for a prolonged period of time over which the active principle is progressively released. Additional uses for bioadhesives include: bioadhesives/mucoadhesives in drug delivery to the gastrointestinal tract; nanoparticles as a gastroadhesive drug delivery system; mucoadhesive buccal patches for peptide delivery; bioadhesive dosage forms for buccal/gingival administration; semisolid dosage forms as buccal bioadhesives; bioadhesive dosage forms for nasal administration; ocular bioadhesive delivery systems; nanoparticles as bioadhesive ocular drug delivery systems; and bioadhesive dosage forms for vaginal and intrauterine applications.

The bioadhesive may also contain liposomes. Liposomes are unilamellar or multilamellar lipid vesicles which entrap a significant fraction of aqueous solution. The vesicular microreservoirs of liposomes can contain a variety of water-soluble materials, which are thus suspended within the emulsion. The preparation of liposomes and the variety of uses of liposomes in biological systems has been disclosed in U.S. Pat. Nos. 4,708,861, 4,224,179, and 4,235,871. Liposomes are generally formed by mixing long chain carboxylic acids, amines, and cholesterol, as well as phospholipids, in aqueous buffers. The organic components spontaneously form multilamellar bilayer structures called liposomes. Depending on their composition and storage conditions, liposomes exhibit varying stabilities. Liposomes serve as models of cell membranes and also are used as drug delivery systems.

Most attempts to use liposomes as drug delivery vehicles have envisioned liposomes as entities which circulate in blood, to be taken up by certain cells or tissues in which their degradation would slowly release their internal aqueous drug-containing contents. In an effort to aid in their up-take by a given target tissue, some liposomes have been "tailored" by binding specific antibodies or antigens to the outer surface. Liposomes have also been devised as controlled release systems for the delivery of their contents in vivo. Compositions in which liposomes containing biologically active agents are maintained and immobilized in polymer matrices, such as methylcellulose, collagen and agarose, for sustained release of the liposome contents, are described in U.S. Pat. No. 4,708,861 to Popescu et al.

In this manner, the present invention contemplates a bioadhesive comprising E-IA produced from PmHAS. The present invention also contemplates a composition containing a bioadhesive comprising HA produced from PmHAS and an effective amount of a medicament, wherein the medicament can be entrapped or grafted directly within the HA bioadhesive or be suspended within a liposome which is entrapped or grafted within the HA bioadhesive. These compositions are especially suited to the controlled release of medicaments.

Such compositions are useful on the tissues, skin, and mucus membranes (mucosa) of an animal body, such as that of a human, to which the compositions adhere. The compositions so adhered to the mucosa, skin, or other tissue slowly release the treating agent to the contacted body area for relatively long periods of time, and cause the treating agent to be sorbed (absorbed or adsorbed) at least at the vicinity of the contacted body area. Such time periods are longer than the time of release for a similar composition that does not include the HA bioadhesive.

The treating agents useful herein are selected generally from the classes of medicinal agents and cosmetic agents. Substantially any agent of these two classes of materials that is a solid at ambient temperatures may be used in a composition or method of the present invention. Treating agents that are liquid at ambient temperatures, e.g. nitroglycerine, can be used in a composition of this invention, but are not preferred because of the difficulties presented in their formulation. The treating agent may be used singly or as a mixture of two or more such agents.

One or more adjuvants may also be included with a treating agent, and when so used, an adjuvant is included in the meaning of the phrase "treating agent" or "medicament." Exemplary of useful adjuvants are chelating agents such as EDTA that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is present in the compositions of this invention in an amount that is sufficient to prevent, cure and/or treat a condition for a desired period of time for which the composition of this invention is to be administered, and such an amount is referred herein as "an effective amount." As is well known, particularly in the medicinal arts, effective amounts of medicinal agents vary with the particular agent involved, the condition being treated and the rate at which the composition containing the medicinal agent is eliminated from the body, as well as varying with the animal in which it is being used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Inasmuch as amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agent for a particular composition of this invention.

The second principle ingredient of this embodiment of the present invention is a bioadhesive comprising an amount of hyaluronic acid (HA) from PmHAS or chondroitin from PmCS. Such a glycosaminoglycan bioadhesive made from a HA or chondroitin chain directly polymerized onto a molecule with the desired pharmacological property or a HA or chondroitin chain polymerized onto a matrix or liposome which in turn contains or binds the medicament.

Although the foregoing invention has been described in some detail by way of illustration and example for purposes of clarity of understanding, it will be obvious to those skilled in the art that certain changes and modifications may be practiced without departing from the spirit and scope thereof; as described in this specification and as defined in the appended claims below.

What I claim is:

1. A method for elongating a hyaluronic acid polymer acceptor, comprising the steps of:

providing a hyaluronic acid polymer acceptor, wherein the hyaluronic acid polymer acceptor has at least two sugar units selected from the group consisting of GlcA and GlcNAc;

providing a hyaluronic acid synthase capable of elongating the hyaluronic acid polymer acceptor, wherein the hyaluronic acid synthase has an amino acid sequence as set forth in SEQ. ID NO:1; and providing UDP-GlcA and UDP-GlcNAc sugars such that the hyaluronic acid synthase elongates the hyaluronic acid polymer acceptor.

2. The method of claim 1, wherein the hyaluronic acid polymer acceptor is attached to a substrate.

3. The method of claim 2, wherein the substrate is a silica or silicon compound.

4. The method of claim 3, wherein the substrate is glass.

5. The method of claim 2, wherein the substrate is a polymer.

6. The method of claim 2, wherein the substrate is an organic compound.

7. A method for elongating a hyaluronic acid polymer acceptor, comprising the steps of:

providing a hyaluronic acid polymer acceptor, wherein the hyaluronic acid polymer acceptor has at least two sugar units selected from the group consisting of GlcA and GlcNAc;

providing a hyaluronic acid synthase capable of elongating the hyaluronic acid polymer acceptor, wherein the hyaluronic acid synthase is encoded by a nucleotide sequence as set forth in SEQ. ID NO: 2; and providing UDP-GlcA and UDP-GlcNAc sugars such that the hyaluronic acid synthase elongates the hyaluronic acid polymer acceptor.

8. The method of claim 7, wherein the hyaluronic acid polymer acceptor is attached to a substrate.

9. The method of claim 8, wherein the substrate is a silica or silicon compound.

10. The method of claim 9, wherein the substrate is glass.

11. The method of claim 8, wherein the substrate is a polymer.

12. The method of claim 8, wherein the substrate is an organic compound.

13. A method for elongating a hyaluronic acid polymer acceptor, comprising the steps of:

providing a hyaluronic acid polymer acceptor, wherein the hyaluronic acid polymer acceptor has at least three sugar units selected from the group consisting of GlcA and GlcNAc;

providing a hyaluronic acid synthase capable of elongating the hyaluronic acid polymer acceptor, wherein the hyaluronic acid synthase has an amino acid sequence as set forth in SEQ. ID NO:1; and providing UDP-GlcA and UDP-GlcNAc sugars such that the hyaluronic acid synthase elongates the hyaluronic acid polymer acceptor.

14. The method of claim 13, wherein the hyaluronic acid polymer acceptor is attached to a substrate.

15. The method of claim 14, wherein the substrate is a silica or silicon compound.

16. The method of claim 15, wherein the substrate is glass.

17. The method of claim 14, wherein the substrate is a polymer.

18. The method of claim 14, wherein the substrate is an organic compound.

19. A method for elongating a hyaluronic acid polymer acceptor, comprising the steps of:

providing a hyaluronic acid polymer acceptor, wherein the hyaluronic acid polymer acceptor has at least three sugar units selected from the group consisting of GlcA and GlcNAc;

providing a hyaluronic acid synthase capable of elongating the hyaluronic acid polymer acceptor, wherein the hyaluronic acid synthase is encoded by a nucleotide sequence as set forth in SEQ. ID NO: 2; and providing UDP-GlcA and UDP-GlcNAc sugars such that the hyaluronic acid synthase elongates the hyaluronic acid polymer acceptor.

20. The method of claim 19, wherein the hyaluronic acid polymer acceptor is attached to a substrate.

21. The method of claim 20, wherein the substrate is a silica or silicon compound.

22. The method of claim 21, wherein the substrate is glass.

23. The method of claim 20, wherein the substrate is a polymer.

24. The method of claim 20, wherein the substrate is an organic compound.

25. A method of making a glycosidic bond between a hyaluronic acid polymer acceptor and at least one of GlcA and GlcNAc, comprising the steps of:

providing a hyaluronic acid synthase capable of making a glycosidic bond between a hyaluronic acid polymer acceptor and at least one of GlcA and GlcNAc, wherein the hyaluronic acid polymer acceptor has at least two sugar units selected from the group consisting of GlcA and GlcNAc and further wherein the hyaluronic acid synthase has an amino acid sequence as set forth in SEQ. ID NO:1; and incubating the hyaluronic acid synthase with at least one of UDP-GlcA and UDP-GlcNAc in the presence of the hyaluronic acid polymer acceptor so as to form the glycosidic bond between the hyaluronic acid polymer acceptor and at least one of GlcA and GlcNAc.

26. The method of claim 25, wherein the hyaluronic acid polymer acceptor is attached to a substrate.

27. The method of claim 26, wherein the substrate is a silica or silicon compound.

28. The method of claim 27, wherein the substrate is glass.

29. The method of claim 26, wherein the substrate is a polymer.

30. The method of claim 26, wherein the substrate is an organic compound.

31. A method of making a glycosidic bond between a hyaluronic acid polymer acceptor and at least one of GlcA and GlcNAc, comprising the steps of:

providing a hyaluronic acid synthase capable of making a glycosidic bond between a hyaluronic acid polymer acceptor and at least one of GlcA and GlcNAc, wherein the hyaluronic acid polymer acceptor has at least two sugar units selected from the group consisting of GlcA and GlcNAc and further wherein the hyaluronic acid synthase is encoded by a nucleotide sequence as set forth in SEQ ID NO: 2; and incubating the hyaluronic acid synthase with at least one of UDP-GlcA and UDP-GlcNAc in the presence of the hyaluronic acid polymer acceptor so as to form the glycosidic bond between the hyaluronic acid polymer acceptor and at least one of GlcA and GlcNAc.

32. The method of claim 31, wherein the hyaluronic acid polymer acceptor is attached to a substrate.

33. The method of claim 32, wherein the substrate is a silica or silicon compound.

34. The method of claim 33, wherein the substrate is glass.

35. The method of claim 32, wherein the substrate is a polymer.

36. The method of claim 32, wherein the substrate is an organic compound.

37. A method of making a glycosidic bond between a hyaluronic acid polymer acceptor and at least one of GlcA and GlcNAc, comprising the steps of:

providing a hyaluronic acid synthase capable of making a glycosidic bond between a hyaluronic acid polymer acceptor and at least one of GlcA and GlcNAc, wherein the hyaluronic acid polymer acceptor has at least three sugar units selected from the group consisting of GlcA and GlcNAc and further wherein the hyaluronic acid synthase has an amino acid sequence as set forth in SEQ. ID NO:1; and incubating the hyaluronic acid synthase with at least one of UDP-GlcA and UDP-GlcNAc inn the presence of the hyaluronic acid polymer acceptor so as to form the glycosidic bond between the hyaluronic acid polymer acceptor and at least one of GlcA and GlcNAc.

38. The method of claim 37, wherein the hyaluronic acid polymer acceptor is attached to a substrate.

39. The method of claim 38, wherein the substrate is a silica or silicon compound.

40. The method of claim 39, wherein the substrate is glass.

41. The method of claim 38, wherein the substrate is a polymer.

42. The method of claim 38, wherein the substrate is an organic compound.

43. A method of making a glycosidic bond between a hyaluronic acid polymer acceptor and at least one of GlcA and GlcNAc, comprising the steps of:

providing a hyaluronic acid synthase capable of making a glycosidic bond between a hyaluronic acid polymer acceptor and at least one of GlcA and GlcNAc, wherein the hyaluronic acid polymer acceptor has at least three sugar units selected from the group consisting of GlcA and GlcNAc and further wherein the hyaluronic acid synthase is encoded by a nucleotide sequence as set forth in SEQ. ID NO: 2; and incubating the hyaluronic acid synthase with at least one of UDP-GlcA and UDP-GlcNAc in the presence of the hyaluronic acid polymer acceptor so as to form the glycosidic bond between the hyaluronic acid polymer acceptor and at least one of GlcA and GlcNAc.

44. The method of claim 43, wherein the hyaluronic acid polymer acceptor is attached to a substrate.

45. The method of claim 44, wherein the substrate is a silica or silicon compound.

46. The method of claim 45, wherein the substrate is glass.

47. The method of claim 44, wherein the substrate is a polymer.

48. The method of claim 44, wherein the substrate is an organic compound.

* * * * *

UNITED STATES PATENT AND TRADEMARK OFFICE
CERTIFICATE OF CORRECTION

PATENT NO. : 6,444,447 B1 
DATED : September 3, 2002
INVENTOR(S) : Paul L. DeAngelis It is certified that error appears in the above-identified patent and that said Letters Patent is hereby corrected as shown below:

Column 2,
Line 39, delete "polysaceharides" and substitute therefore -- polysaccharides --.

Column 3,
Line 8, delete second occurrence of ".".
Line 17, delete "an(liogenesis" and substitute therefore -- angiogenesis --.
Line 32, delete "multocidta" and substitute therefore -- multocida --.
Line 55, delete "Xenopus" and substitute therefore -- *Xenopus* --.
Line 66, delete "Sank" and substitute therefore -- flank --.

Column 4,
Line 35, delete "biodhesive" and substitute therefore -- bioadhesive --.

Column 5,
Lines 13-14, delete "oligosaecharides" and substitute therefore -- oligosaccharides --.
Lines 15 and 21, delete "oligosaceharides" and substitute therefore -- oligosaccharides --.
Line 34, delete "is".
Lines 37 and 46, delete "on".
Line 43, delete "allows" and substitute therefore -- allow --.
Line 60, delete ": naturally" and substitute therefore -- . Naturally --.

Column 6,
Line 5, delete "devices" and substitute therefore -- devices' --.
Lines 20, 28, 37 and 66, delete "PmHAS-D" and substitute therefore -- PmHAS --.
Line 22, insert -- the -- after "of" and before "HA".
Line 34, insert -- a -- after the first occurrence of the word "of" and before "first".
Line 49, insert -- the -- after "for".

Column 7,
Lines 10, 36 and 48, delete "PmHAS-D" and substitute therefore -- PmHAS --.

Column 8,
Line 21, delete "practitioners" and substitute therefore -- practitioners' --.
Line 30, delete "(I) lie" and substitute therefore -- (I) Ile --.
Line 31, delete first occurrence of "(".
Line 37, delete "fables" and substitute therefore -- Tables --.
Line 57, delete the numeral "1" and substitute therefore -- I --.

UNITED STATES PATENT AND TRADEMARK OFFICE
CERTIFICATE OF CORRECTION

PATENT NO. : 6,444,447 B1
DATED : September 3, 2002
INVENTOR(S) : Paul L. DeAngelis It is certified that error appears in the above-identified patent and that said Letters Patent is hereby corrected as shown below:

Column 9,
Line 17, delete ":" and substitute therefore -- . --.
Line 40, delete ".".

Column 11,
Line 1, delete "-".
Lines 4 and 32, delete ".".
Line 6, delete "the" and substitute therefore -- The --.
Line 34, delete "off" and substitute therefore -- of --.
Line 35, delete "actors" and substitute therefore -- factors --.

Column 13,
Line 9, delete "naturally -occurring" and substitute therefore -- naturally-occurring --.
Line 18, delete "C." and substitute therefore -- C --.
Line 26, delete "A;".

Column 14,
Line 6, delete "polysaceharide product." and substitute therefore -- polysaccharide product --.
Lines 24-25 and 36, delete "oligosaceharides" and substitute therefore -- oligosaccharides --.

Column 15,
Line 57, delete "*.E coli*" and substitute therefore -- *E. coli* --.

Column 16,
Line 48, delete "4.4." and substitute therefore -- 4.4 --.
Line 61, delete "(50-250" and substitute therefore -- (~50-250 --.

Column 17,
Line 1, delete "0.5" and substitute therefore -- ~0.5 --.
Line 4, delete "PmHAS-D" and substitute therefore -- PmHAS --.
Line 23, delete "priorto" and substitute therefore -- prior to --.

Column 18,
Line 23, delete "Xenopous DCG42" and substitute therefore -- *Xenopus* DG42 --.
Line 31, delete "PmHAS-D" and substitute therefore -- PmHAS --.

UNITED STATES PATENT AND TRADEMARK OFFICE

CERTIFICATE OF CORRECTION

PATENT NO. : 6,444,447 B1 
DATED : September 3, 2002
INVENTOR(S) : Paul L. DeAngelis It is certified that error appears in the above-identified patent and that said Letters Patent is hereby corrected as shown below:

Column 19,
Line 10, delete "HΛ4," and substitute therefore -- HA4, --.
Line 17, delete "Λ lane" and substitute therefore -- A lane --.
Line 34, delete "E. coil" and substitute therefore -- E. coli --.
Line 43, italicize the word -- *Xenopus* --.
Line 48, delete "Streptococclus" and substitute therefore -- Streptococcus --.
Line 51, delete "C." and substitute therefore -- C --.
Lines 64-65, delete "trifluoroacctic" and substitute therefore -- trifluoroacetic --.

Column 20,
Line 2, delete "Voyagera" and substitute therefore -- Voyager --.
Line 9, delete "oligosaccharides." and substitute therefore -- oligosaccharides, --.
Line 14, delete "C." and substitute therefore -- C --.
Line 26, delete "oligosaccharidcs" and substitute therefore -- oligosaccharides --.
Line 50, delete ",".
Line 60, italicize the word -- *tac* --.

Column 21,
Line 24, delete "*E. Coli*" and substitute therefore -- *E. coli* --.
Line 42, italicize the word -- *Pfu* --.

Column 22,
Line 3, delete "." and substitute therefore -- , --.
Line 6, delete second occurrence of "." and substitute therefore -- , --.
Line 23, delete "." and substitute therefore -- , --.

Column 23,
Line 67, delete "while-preventing" and substitute therefore -- while preventing --.

Column 24,
Line 20, delete first occurrence of "."
Lines 38, 49 and 65, delete "PmHAS-D" and substitute therefore -- PmHAS --.
Line 42, delete "C." and substitute therefore -- C --.
Line 51, delete "Tris. pH 7.2, at 30° C." and substitute therefore -- Tris, pH 7.2, at 30° C --.

Column 24,
Line 50, delete "$F^{moc}$" and substitute therefore -- FMOC --.

UNITED STATES PATENT AND TRADEMARK OFFICE

CERTIFICATE OF CORRECTION

PATENT NO. : 6,444,447 B1
DATED : September 3, 2002
INVENTOR(S) : Paul L. DeAngelis It is certified that error appears in the above-identified patent and that said Letters Patent is hereby corrected as shown below:

Column 25,
Line 37, insert -- to -- after “used” and before “randomly”.
Line 55, delete “C.” and substitute therefore -- C --.
Line 58, delete “H-IA” and substitute therefore -- HA --.

Column 28,
Line 2, delete “.”.
Line 6, delete “Hcalon” and substitute therefore -- Healon --.
Line 14, delete “1993 Dec;27(4)257-61.” and substitute therefore -- 1993 Dec;27(4):257-61 --.
Line 31, insert -- , -- after “healing” and before “the”.
Line 39, delete “.”.

Column 29,
Line 66, delete “.” and substitute therefore -- , --.

Column 30,
Line 7, delete “intercellularjunctions” and substitute therefore -- intercellular junctions --.
Line 61, delete “E-IA” and substitute therefore -- HA --.

Column 48,
Line 13, delete “inn” and substitute therefore -- in --.

Signed and Sealed this

Thirteenth Day of September, 2005

JON W. DUDAS
*Director of the United States Patent and Trademark Office*

SEQUENCE LISTING

```
<160> NUMBER OF SEQ ID NOS:  6

<210> SEQ ID NO 1
<211> LENGTH: 702
<212> TYPE: PRT
<213> ORGANISM: Pasteurella multocida

<400> SEQUENCE: 1

Met Asn Thr Leu Ser Gln Ala Ile Lys Ala Tyr Asn Ser Asn Asp Tyr
  1               5                  10                  15

Gln Leu Ala Leu Lys Leu Phe Glu Lys Ser Ala Glu Ile Tyr Gly Arg
             20                  25                  30

Lys Ile Val Glu Phe Gln Ile Thr Lys Cys Gln Glu Lys Leu Ser Ala
         35                  40                  45

His Pro Ser Val Asn Ser Ala His Leu Ser Val Asn Lys Glu Glu Lys
     50                  55                  60

Val Asn Val Cys Asp Ser Pro Leu Asp Ile Ala Thr Gln Leu Leu Leu
 65                  70                  75                  80

Ser Asn Val Lys Lys Leu Val Leu Ser Asp Ser Glu Lys Asn Thr Leu
                 85                  90                  95

Lys Asn Lys Trp Lys Leu Leu Thr Glu Lys Lys Ser Glu Asn Ala Glu
            100                 105                 110
```

-continued

```
Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Ala Asn Tyr Ile Gln Arg Cys Val Asp Ser Ala Leu Asn Gln
    450                 455                 460

Thr Val Val Asp Leu Glu Val Cys Ile Cys Asn Asp Gly Ser Thr Asp
465                 470                 475                 480

Asn Thr Leu Glu Val Ile Asn Lys Leu Tyr Gly Asn Asn Pro Arg Val
                485                 490                 495

Arg Ile Met Ser Lys Pro Asn Gly Gly Ile Ala Ser Ala Ser Asn Ala
            500                 505                 510

Ala Val Ser Phe Ala Lys Gly Tyr Tyr Ile Gly Gln Leu Asp Ser Asp
        515                 520                 525

Asp Tyr Leu Glu Pro Asp Ala Val Glu Leu Cys Leu Lys Glu Phe Leu
```

-continued

```
    530                 535                 540

Lys Asp Lys Thr Leu Ala Cys Val Tyr Thr Thr Asn Arg Asn Val Asn
545                 550                 555                 560

Pro Asp Gly Ser Leu Ile Ala Asn Gly Tyr Asn Trp Pro Glu Phe Ser
                565                 570                 575

Arg Glu Lys Leu Thr Thr Ala Met Ile Ala His His Phe Arg Met Phe
            580                 585                 590

Thr Ile Arg Ala Trp His Leu Thr Asp Gly Phe Asn Glu Lys Ile Glu
        595                 600                 605

Asn Ala Val Asp Tyr Asp Met Phe Leu Lys Leu Ser Glu Val Gly Lys
    610                 615                 620

Phe Lys His Leu Asn Lys Ile Cys Tyr Asn Arg Val Leu His Gly Asp
625                 630                 635                 640

Asn Thr Ser Ile Lys Lys Leu Gly Ile Gln Lys Lys Asn His Phe Val
                645                 650                 655

Val Val Asn Gln Ser Leu Asn Arg Gln Gly Ile Thr Tyr Tyr Asn Tyr
            660                 665                 670

Asp Glu Phe Asp Asp Leu Asp Glu Ser Arg Lys Tyr Ile Phe Asn Lys
        675                 680                 685

Thr Ala Glu Tyr Gln Glu Glu Ile Asp Ile Leu Lys Asp Ile
    690                 695                 700


<210> SEQ ID NO 2
<211> LENGTH: 2112
<212> TYPE: DNA
<213> ORGANISM: Pasteurella multocida

<400> SEQUENCE: 2

atgaatacat tatcacaagc aataaaagca tataacagca atgactatca attagcactc     60

aaattatttg aaaagtcggc ggaaatctat ggacggaaaa ttgttgaatt tcaaattacc    120

aaatgccaag aaaaactctc agcacatcct tctgttaatt cagcacatct ttctgtaaat    180

aaagaagaaa aagtcaatgt ttgcgatagt ccgttagata ttgcaacaca actgttactt    240

tccaacgtaa aaaaattagt actttctgac tcggaaaaaa acacgttaaa aaataaatgg    300

aaattgctca ctgagaagaa atctgaaaat gcggaggtaa gagcggtcgc ccttgtacca    360

aaagattttc ccaaagatct ggttttagcg cctttacctg atcatgttaa tgattttaca    420

tggtacaaaa agcgaaagaa aagacttggc ataaaacctg aacatcaaca tgttggtctt    480

tctattatcg ttacaacatt caatcgacca gcaattttat cgattacatt agcctgttta    540

gtaaaccaaa aaacacatta cccgtttgaa gttatcgtga cagatgatgg tagtcaggaa    600

gatctatcac cgatcattcg ccaatatgaa aataaattgg atattcgcta cgtcagacaa    660

aaagataacg gttttcaagc cagtgccgct cggaatatgg gattacgctt agcaaaatat    720

gactttattg gcttactcga ctgtgatatg gcgccaaatc cattatgggt tcattcttat    780

gttgcagagc tattagaaga tgatgattta acaatcattg gtccaagaaa atacatcgat    840

acacaacata ttgacccaaa agacttctta aataacgcga gtttgcttga atcattacca    900

gaagtgaaaa ccaataatag tgttgccgca aaaggggaag gaacagtttc tctggattgg    960

cgcttagaac aattcgaaaa aacagaaaat ctccgcttat ccgattcgcc tttccgtttt   1020

tttgcggcgg gtaatgttgc tttcgctaaa aaatggctaa ataaatccgg tttctttgat   1080

gaggaattta atcactgggg tggagaagat gtggaatttg gatatcgctt attccgttac   1140

ggtagtttct ttaaaactat tgatggcatt atggcctacc atcaagagcc accaggtaaa   1200
```

-continued

```
gaaaatgaaa ccgatcgtga agcgggaaaa aatattacgc tcgatattat gagagaaaag   1260

gtcccttata tctatagaaa acttttacca atagaagatt cgcatatcaa tagagtacct   1320

ttagtttcaa tttatatccc agcttataac tgtgcaaact atattcaacg ttgcgtagat   1380

agtgcactga atcagactgt tgttgatctc gaggtttgta tttgtaacga tggttcaaca   1440

gataatacct tagaagtgat caataagctt tatggtaata atcctagggt acgcatcatg   1500

tctaaaccaa atggcggaat agcctcagca tcaaatgcag ccgtttcttt tgctaaaggt   1560

tattacattg ggcagttaga ttcagatgat tatcttgagc ctgatgcagt tgaactgtgt   1620

ttaaaagaat tttaaaaaga taaaacgcta gcttgtgttt ataccactaa tagaaacgtc   1680

aatccggatg gtagcttaat cgctaatggt tacaattggc cagaattttc acgagaaaaa   1740

ctcacaacgg ctatgattgc tcaccacttt agaatgttca cgattagagc ttggcattta   1800

actgatggat tcaatgaaaa aattgaaaat gccgtagact atgacatgtt cctcaaactc   1860

agtgaagttg gaaaatttaa acatcttaat aaaatctgct ataaccgtgt attacatggt   1920

gataacacat caattaagaa acttggcatt caaaagaaaa accattttgt tgtagtcaat   1980

cagtcattaa atagacaagg cataacttat tataattatg acgaatttga tgatttagat   2040

gaaagtagaa agtatatttt caataaaacc gctgaatatc aagaagagat tgatatctta   2100

aaagatattt aa                                                       2112
```

<210> SEQ ID NO 3
<211> LENGTH: 965
<212> TYPE: PRT
<213> ORGANISM: Pasteurella multocida

<400> SEQUENCE: 3

```
Met Asn Thr Leu Ser Gln Ala Ile Lys Ala Tyr Asn Ser Asn Asp Tyr
  1               5                  10                  15

Glu Leu Ala Leu Lys Leu Phe Glu Lys Ser Ala Glu Thr Tyr Gly Arg
             20                  25                  30

Lys Ile Val Glu Phe Gln Ile Ile Lys Cys Lys Glu Lys Leu Ser Thr
         35                  40                  45

Asn Ser Tyr Val Ser Glu Asp Lys Lys Asn Ser Val Cys Asp Ser Ser
     50                  55                  60

Leu Asp Ile Ala Thr Gln Leu Leu Leu Ser Asn Val Lys Lys Leu Thr
 65                  70                  75                  80

Leu Ser Glu Ser Glu Lys Asn Ser Leu Lys Asn Lys Trp Lys Ser Ile
                 85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205
```

-continued

```
Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Asn Pro Ser Ile Thr
    290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Val Ala
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
    370                 375                 380

Ala Ile His Gln Glu Pro Pro Gly Lys Glu Asn Glu Thr Glu Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620
```

-continued

```
Ile Cys Tyr Asn Arg Val Leu His Gly Asp Asn Thr Ser Ile Lys Lys
625                 630                 635                 640

Leu Gly Ile Gln Lys Lys Asn His Phe Val Val Val Asn Gln Ser Leu
                645                 650                 655

Asn Arg Gln Gly Ile Asn Tyr Tyr Asn Tyr Asp Lys Phe Asp Asp Leu
            660                 665                 670

Asp Glu Ser Arg Lys Tyr Ile Phe Asn Lys Thr Ala Glu Tyr Gln Glu
        675                 680                 685

Glu Met Asp Met Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720

Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
            740                 745                 750

Ile Leu Ala Phe Tyr His Lys His Gln Val Asn Ile Leu Leu Asn Asn
        755                 760                 765

Asp Ile Ser Tyr Tyr Thr Ser Asn Arg Leu Ile Lys Thr Glu Ala His
    770                 775                 780

Leu Ser Asn Ile Asn Lys Leu Ser Gln Leu Asn Leu Asn Cys Glu Tyr
785                 790                 795                 800

Ile Ile Phe Asp Asn His Asp Ser Leu Phe Val Lys Asn Asp Ser Tyr
                805                 810                 815

Ala Tyr Met Lys Lys Tyr Asp Val Gly Met Asn Phe Ser Ala Leu Thr
            820                 825                 830

His Asp Trp Ile Glu Lys Ile Asn Ala His Pro Pro Phe Lys Lys Leu
        835                 840                 845

Ile Lys Thr Tyr Phe Asn Asp Asn Asp Leu Arg Ser Met Asn Val Lys
    850                 855                 860

Gly Ala Ser Gln Gly Met Phe Met Lys Tyr Ala Leu Pro His Glu Leu
865                 870                 875                 880

Leu Thr Ile Ile Lys Glu Val Ile Thr Ser Cys Gln Ser Ile Asp Ser
                885                 890                 895

Val Pro Glu Tyr Asn Thr Glu Asp Ile Trp Phe Gln Phe Ala Leu Leu
            900                 905                 910

Ile Leu Glu Lys Lys Thr Gly His Val Phe Asn Lys Thr Ser Thr Leu
        915                 920                 925

Thr Tyr Met Pro Trp Glu Arg Lys Leu Gln Trp Thr Asn Glu Gln Ile
    930                 935                 940

Gln Ser Ala Lys Lys Gly Glu Asn Ile Pro Val Asn Lys Phe Ile Ile
945                 950                 955                 960

Asn Ser Ile Thr Leu
                965
```

<210> SEQ ID NO 4
<211> LENGTH: 2979
<212> TYPE: DNA
<213> ORGANISM: Pasteurella multocida

<400> SEQUENCE: 4

```
ttataaactg attaaagaag gtaaacgatt caagcaaggt taatttttaa aggaaagaaa      60

atgaatacat tatcacaagc aataaaagca tataacagca atgactatga attagcactc     120

aaattatttg agaagtctgc tgaaacctac gggcgaaaaa tcgttgaatt ccaaattatc     180
```

-continued

```
aaatgtaaag aaaaactctc gaccaattct tatgtaagtg aagataaaaa aaacagtgtt    240
tgcgatagct cattagatat cgcaacacag ctcttacttt ccaacgtaaa aaaattaact    300
ctatccgaat cagaaaaaaa cagtttaaaa aataaatgga aatctatcac tgggaaaaaa    360
tcggagaacg cagaaatcag aaaggtggaa ctagtaccca aagattttcc taaagatctt    420
gttcttgctc cattgccaga tcatgttaat gattttacat ggtacaaaaa tcgaaaaaaa    480
agcttaggta taaagcctgt aaataagaat atcggtcttt ctattattat tcctacattt    540
aatcgtagcc gtattttaga tataacgtta gcctgtttgg tcaatcagaa aacaaactac    600
ccatttgaag tcgttgttgc agatgatggt agtaaggaaa acttacttac cattgtgcaa    660
aaatacgaac aaaaacttga cataaagtat gtaagacaaa aagattatgg atatcaattg    720
tgtgcagtca gaaacttagg tttacgtaca gcaaagtatg attttgtctc gattctagac    780
tgcgatatgg caccacaaca attatgggtt cattcttatc ttacagaact attagaagac    840
aatgatattg ttttaattgg acctagaaaa tatgtggata ctcataatat taccgcagaa    900
caattcctta acgatccata tttaatagaa tcactacctg aaaccgctac aaataacaat    960
ccttcgatta catcaaaagg aaatatatcg ttggattgga gattagaaca tttcaaaaaa   1020
accgataatc tacgtctatg tgattctccg tttcgttatt ttgttgcggg taatgttgca   1080
ttttctaaag aatggctaaa taaagtaggt tggttcgatg aagaatttaa tcattggggg   1140
ggcgaagatg tagaatttgg ttacagatta tttgccaaag gctgtttttt cagagtaatt   1200
gacggcggaa tggccatcca tcaagaacca cctggtaaag aaaatgaaac agaacgcgaa   1260
gctggtaaaa gtattacgct taaaattgtg aaagaaaagg taccttacat ctatagaaag   1320
cttttaccaa tagaagattc acatattcat agaatacctt tagtttctat ttatatcccc   1380
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccattttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatatgttaa aagatcttaa actcattcaa   2160
aataaagatg ccaaaatcgc agtcagtatt ttctatccca atacattaaa cggcttagtg   2220
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcatttttg ataatcatga cagcctattc gttaaaaatg acagctatgc ttatatgaaa   2520
```

-continued

```
aaatatgatg tcggcatgaa tttctcagca ttaacacatg attggatcga gaaaatcaat   2580

gcgcatccac catttaaaaa gctgattaaa acctatttta atgacaatga cttaagaagt   2640

atgaatgtga aggggcatc acaaggtatg tttatgaagt atgcgctacc gcatgagctt   2700

ctgacgatta ttaaagaagt catcacatcc tgccaatcaa ttgatagtgt gccagaatat   2760

aacactgagg atatttggtt ccaatttgca cttttaatct tagaaaagaa aaccggccat   2820

gtatttaata aaacatcgac cctgacttat atgccttggg aacgaaaatt acaatggaca   2880

aatgaacaaa ttcaaagtgc aaaaaaaggc gaaaatatcc ccgttaacaa gttcattatt   2940

aatagtataa cgctataaaa catttgcatt ttattaaaa                          2979


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: motif
<221> NAME/KEY: MOD_RES
<222> LOCATION: (1)
<223> OTHER INFORMATION: Xaa = Asp or Asn
<221> NAME/KEY: MOD_RES
<222> LOCATION: (5)
<223> OTHER INFORMATION: Xaa = Ser or Thr

<400> SEQUENCE: 5

Xaa Asp Gly Ser Xaa
  1               5


<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: motif
<221> NAME/KEY: MOD_RES
<222> LOCATION: (4)
<223> OTHER INFORMATION: Xaa = Asp or Thr

<400> SEQUENCE: 6

Asp Ser Asp Xaa Tyr
  1               5
```